(12) United States Patent
Hill et al.

(10) Patent No.: US 10,625,004 B2
(45) Date of Patent: Apr. 21, 2020

(54) LACTATION SYSTEM AND METHOD

(71) Applicant: Regents of the University of Minnesota, Minneapolis, MN (US)

(72) Inventors: Courtney Hill, Minneapolis, MN (US); Christie Traczyk, Savage, MN (US); Hannah Bearinger, Saint Paul, MN (US); Jarrod Neuharth, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/956,498

(22) Filed: Apr. 18, 2018

(65) Prior Publication Data

US 2018/0296741 A1   Oct. 18, 2018

Related U.S. Application Data

(60) Provisional application No. 62/486,812, filed on Apr. 18, 2017.

(51) Int. Cl.
*A61M 1/06* (2006.01)
*A41D 1/215* (2018.01)
(Continued)

(52) U.S. Cl.
CPC .............. *A61M 1/062* (2014.02); *A41C 3/04* (2013.01); *A41D 1/215* (2018.01); *A61M 1/06* (2013.01);
(Continued)

(58) Field of Classification Search
None
See application file for complete search history.

(56) References Cited

U.S. PATENT DOCUMENTS 5,810,772 A * 9/1998 Niederberger .......... A61M 1/06
604/346
6,247,996 B1 * 6/2001 Fields ...................... A41C 3/04
450/36
(Continued)

OTHER PUBLICATIONS

International Search Report and Written Opinion, Application No. PCT/US2018/028162, dated Jul. 3, 2018, 12 pages.
(Continued)

*Primary Examiner* — Bhisma Mehta
*Assistant Examiner* — Matthew A Engel
(74) *Attorney, Agent, or Firm* — Patterson Thuente Pedersen, P.A.

(57) ABSTRACT

A lactation system is disclosed. Embodiments include at least one extraction mechanism including a compression mechanism and a collection mechanism, and a controller. The compression mechanism can include a plurality of manipulable members, each operably coupled to an actuator and arrangeable circumferentially about a breast of a user such that each member can be actuated to selectively apply pressure to a region of the breast. The collection mechanism can be removably coupleable to the compression mechanism and can comprise a storage compartment to receive and store milk The controller can be operably coupleable to the actuators to cause the members to move according to a movement pattern which can be configured to stimulate the breast to induce the flow of milk from the breast and modulated based on sensor feedback. A wearable garment with an inner structure can be removably coupled to the extraction mechanism. An outer cover can be arrangeable to conceal the extraction mechanism.

9 Claims, 28 Drawing Sheets

(51) Int. Cl.
*A41C 3/04* (2006.01)
*A61F 7/00* (2006.01)

(52) U.S. Cl.
CPC ............. *A61F 2007/0021* (2013.01); *A61M 2205/0266* (2013.01); *A61M 2205/103* (2013.01); *A61M 2205/3334* (2013.01); *A61M 2205/3368* (2013.01); *A61M 2205/3576* (2013.01); *A61M 2205/3613* (2013.01); *A61M 2205/3653* (2013.01); *A61M 2205/502* (2013.01); *A61M 2230/60* (2013.01); *A61M 2230/62* (2013.01)

(56) References Cited

U.S. PATENT DOCUMENTS

| | | | | |
|---|---|---|---|---|
| 6,358,226 | B1* | 3/2002 | Ryan | A61M 1/062 604/113 |
| 6,471,660 | B1* | 10/2002 | Covington | A61K 49/0004 435/7.23 |
| 7,811,248 | B2* | 10/2010 | Bjorge | A61M 1/064 2/267 |
| 8,801,495 | B1* | 8/2014 | Guindon | A41C 3/105 450/36 |
| 9,539,377 | B2* | 1/2017 | Makower | A61M 1/064 |
| 9,616,156 | B2* | 4/2017 | Alvarez | A61M 1/06 |
| 10,046,097 | B2* | 8/2018 | Thompson | A61M 1/06 |
| 10,105,474 | B2* | 10/2018 | Barral | A61B 5/4857 |
| 2001/0044593 | A1* | 11/2001 | Lundy | A61M 1/062 604/74 |
| 2003/0191433 | A1* | 10/2003 | Prentiss | A61M 1/06 604/74 |
| 2003/0211810 | A1* | 11/2003 | Raimondo | A41C 3/04 450/36 |
| 2005/0234370 | A1* | 10/2005 | Beal | A61H 9/0078 601/15 |
| 2006/0106334 | A1* | 5/2006 | Jordan | A61M 1/0027 604/74 |
| 2006/0247559 | A1* | 11/2006 | Fei | A61H 9/005 601/15 |
| 2006/0270973 | A1* | 11/2006 | Chu | A61H 9/0078 604/74 |
| 2008/0208116 | A1* | 8/2008 | Dao | A61M 1/06 604/74 |
| 2008/0262420 | A1* | 10/2008 | Dao | A61M 1/06 604/74 |
| 2008/0275386 | A1* | 11/2008 | Myers | A61M 1/0068 604/74 |
| 2008/0287037 | A1* | 11/2008 | Solberg | A61M 1/06 450/36 |
| 2010/0159802 | A1* | 6/2010 | Abbaszadeh | A41C 3/04 450/36 |
| 2012/0004603 | A1* | 1/2012 | Harari | A61B 5/1075 604/74 |
| 2013/0023821 | A1* | 1/2013 | Khalil | A61M 1/064 604/74 |
| 2013/0096461 | A1* | 4/2013 | Sella | A61M 1/06 600/573 |
| 2014/0121593 | A1* | 5/2014 | Felber | A61M 1/06 604/74 |
| 2014/0142501 | A1* | 5/2014 | Clark | A61M 1/066 604/74 |
| 2014/0188199 | A1* | 7/2014 | Enderby | A61F 7/08 607/108 |
| 2014/0364036 | A1* | 12/2014 | Abbaszadeh | A61M 1/062 450/36 |
| 2014/0378946 | A1 | 12/2014 | Thompson | |
| 2015/0065994 | A1* | 3/2015 | Fridman | A61M 1/06 604/514 |
| 2016/0206794 | A1* | 7/2016 | Makower | A61M 1/062 |
| 2016/0287768 | A1* | 10/2016 | Powell | A61M 1/064 |
| 2017/0112983 | A1* | 4/2017 | Thorne | A61M 1/06 |
| 2019/0240386 | A1* | 8/2019 | Larsson | A61M 1/0037 |

OTHER PUBLICATIONS

Defrin et al., Quantitative somatosensory testing of warm and heat-pain thresholds: the effect of body region and testing method. Clin J Pain. Feb. 2006; 22(2):130-6.

Elad et al., Biomechanics of milk extraction during breast-feeding. Proc Natl Acad Sci U S A. Apr. 8, 2014; 111(14):5230-5.

Geddes et al., Tongue movement and intra-oral vacuum in breastfeeding infants. Early Hum Dev. Jul. 2008; 84(7):471-7.

Kent et al., Effect of warm breastshields on breast milk pumping. J Hum Lact. Nov. 2011; 27(4):331-8.

Yokoyama et al., Releases of oxytocin and prolactin during breast massage and suckling in puerperal women. European Journal of Obstetrics & Gynecology and Reproductive Biology 53 (1994) 17-20.

\* cited by examiner

SECTION A-A

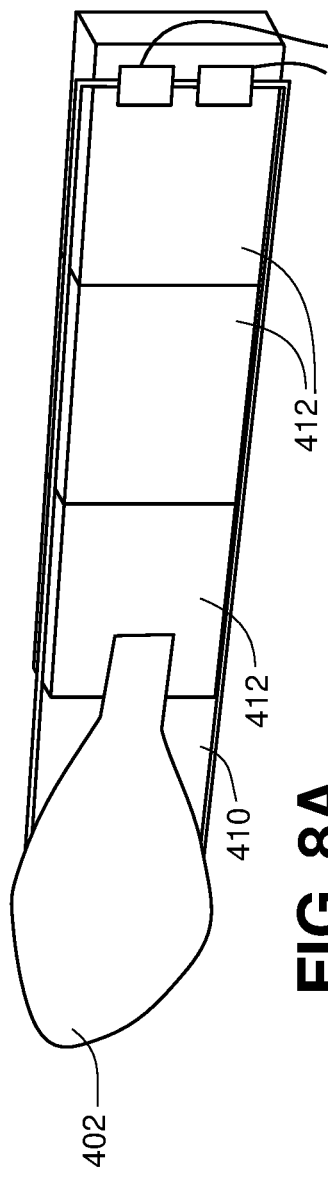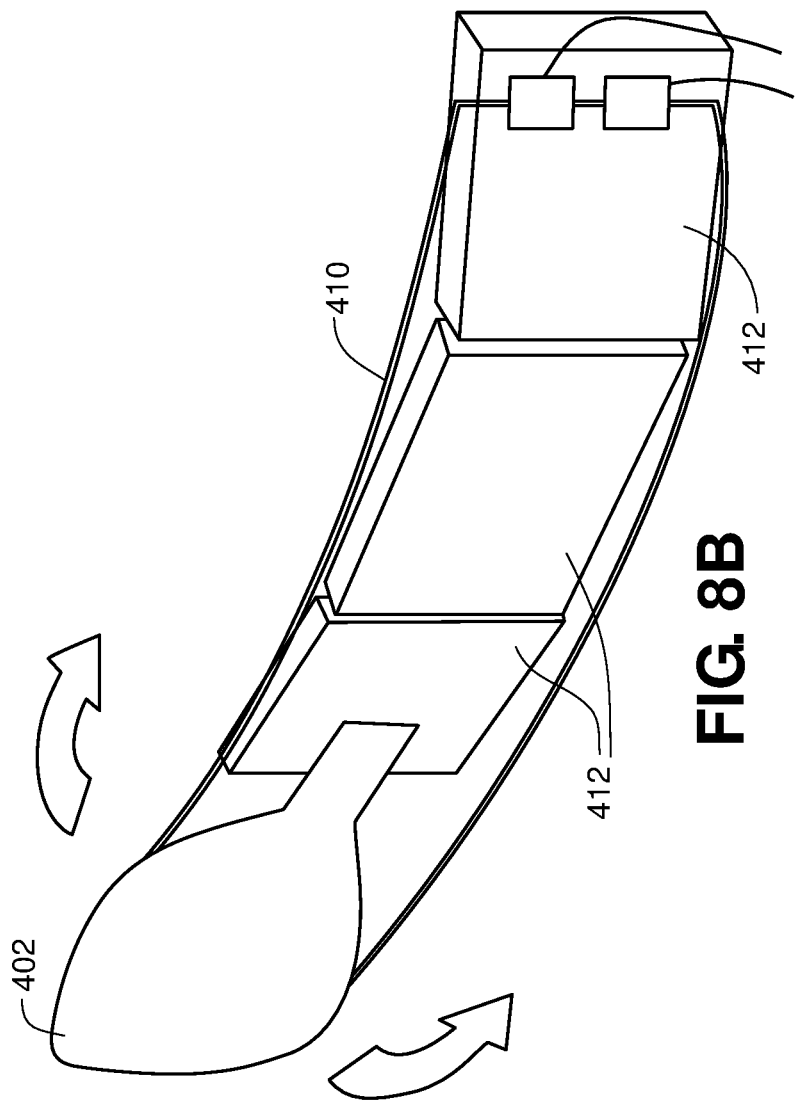
FIG. 8A
FIG. 8B

LACTATION SYSTEM AND METHOD

CROSS-REFERENCE TO RELATED APPLICATION

The present disclosure claims the benefit of U.S. Provisional Patent Application No. 62/486,812, filed Apr. 18, 2017, the disclosure of which is incorporated by reference herein.

TECHNICAL FIELD

Embodiments of the present disclosure relate generally to the field of lactation systems, and more particularly to electrically-powered breast milk extraction and collection systems.

BACKGROUND

Breast milk is a source of nutrition for many human infants. Breast milk is recommended as a source of nutrition for infants by the World Health Organization, the Centers for Disease Control and the American Academy of Pediatrics. In addition to purported health benefits for the nursing mother and child, direct nursing can be a cheap or cost-free method of feeding an infant. In direct nursing, the suckling action of the infant's mouth can induce the release of oxytocin into the bloodstream. Oxytocin can make the muscles around the mammary glands in the breasts contract, pushing milk into the milk ducts and out through nipple openings in what is known as the milk ejection reflex. The milk ejection reflex starts a flow of milk that can be consumed by the infant.

Direct nursing is not always possible or preferable for the mother or child. Even when mothers are physically capable of nursing, direct nursing requires the mother to be available to feed the infant multiple times per day. In addition, the mother's milk production schedule may not be optimal for the infant's needs. Breast pumping technology has enabled mothers to express milk for storage and later feeding. The infant can be fed stored milk when needed by the mother, a non-birthing parent, or a caregiver. Milk storage can also provide human breast milk to infants who are unable to receive it from their birth mothers (for example, in cases of adoption, or undersupply).

Conventional breast pumps rely on a suction mechanism provided by a powered vacuum or hand pump. These pumps generally comprise a roughly hemi-spherical dome that can be placed over the nipple-areolar complex and a tube or other conduit for expressed milk to be pumped from the breast to a collection mechanism (such as a bottle, jar, or pouch). One disadvantage of conventional breast pumps is the need to disrobe sufficiently to expose the nipple. In addition, while hand-powered pumps can be quiet, they are generally slow, and require a significant amount of physical exertion by the user. Electrically powered breast pumps can be faster (especially those that are capable of expressing milk from both breasts simultaneously), but are often undesirably noisy. Users therefore often require a private space in which to pump, and are generally prevented or distracted from other activities during the pumping process. Furthermore, suction-based pumps can produce up to ten times the amount of suction that an infant applies while suckling. This increased level of suction often leads to discomfort and pain.

Another method for expressing breast milk is known as manual expression. Instead of the suction action of a pump, the hands are used to applying pressure to the breast tissue in patterns that induce the flow of milk, which can be collected in a container. In addition to cost, manual (or "hand") expression can be advantageous because pressure can be applied selectively to focus on particular areas of the breast. Many women have particular areas of the breast that are more productive of milk, and these areas can change over time. Manual expression is also thought to affect the nutritional content of the milk. Studies have shown that hand expressed milk has higher fat concentrations than suction pump expressed milk. This may be due to a retrograde milk flow within the breast. Milk can flow from the breast, toward the chest wall, before exiting at the nipple-areolar complex. This retrograde flow, which is presumed to be enabled by an infant's suckling pattern, can allow for the backwash of milk into the originating alveoli which can carry the higher density milk that contains higher fat concentrations.

SUMMARY

Embodiments of the present disclosure provide systems and methods for assisting lactation without requiring application of a vacuum for milk extraction. The system can include elements configured to deliver a sequence of manipulations that provide physical compression to the breast tissue. The manipulations can be modulated (in force, rate, range, or other parameters) in a manner to deliver a desired flow rate of milk. The manipulations can be tailored mimic the behavior of a suckling infant. In embodiments, a sensor can provide a feedback signal to a control mechanism that can modulate actuator(s) to allow automated adjustment of manipulations in order to provide the desired milk production. The system can be integrated within a wearable garment such that the user does not need to disrobe during use.

Embodiments of the present disclosure include a lactation system that comprises a wearable garment with an inner structure configured to be removably coupled to at least one insert and an outer cover comprising padding and arrangeable to conceal the at least one insert. Each insert can include a compression mechanism comprising a plurality of manipulable members, with each member operably coupled to an actuator. The members can be arrangeable circumferentially about the breast such that each member can be actuated to selectively apply pressure to a region of the breast. The insert can further include a collection mechanism, operably coupleable to the compression mechanism proximate a nipple of the user with a storage compartment to receive and store a flow of milk from the breast. Each insert can further comprise a cover configured to separate the insert from the skin of the user.

The controller can be operably coupleable to the actuators to cause the members to move according to a movement pattern, the movement pattern can be configured to stimulate the breast to induce the flow of milk from the breast. The induced flow of milk can be at least partially retrograde.

The lactation system can further include a stimulation mechanism comprising a heating element configured to warm mammary glands within the breast to a temperature between 35° Celsius and 42° Celsius. The stimulation mechanism can comprise a plurality of heating elements arranged in the outer cover.

In embodiments, the movement pattern can comprise mechanically compressing the breast at a pressure between 0 mmHg and 215 mmHg, with an average of between about 20 mmHg and 40 mmHg. The movement pattern can comprise mechanically compressing the breast in a burst pattern including applying pressure to locations at opposite positions around the breast. The burst pattern can comprise repeatedly applying an upper pressure of about 200 mmHg for about one second and a lower pressure of about 20 mmHg for about three to seven seconds, or about two to four seconds. The burst pattern can be repeated about five times.

Embodiments can include at least one sensor for detecting the flow of milk, at least one sensor for detecting the strain or displacement of the breast, and at least one sensor for detecting the temperature of the mammary glands within the breast. The controller can be configured to modify the movement pattern based on at least the flow of milk, the strain or displacement of the breast, and/or the temperature of the mammary glands within the breast. In embodiments the movement pattern can be modified by modifying the timing and magnitude of pressure applied to the locations.

In embodiments, the members can operably coupleable to an annular base that is arrangeable about the breast proximate the chest wall of the user. Each of the members can further be rotatable about an individual axis. In embodiments, each actuator comprises at least one shape-memory alloy element configured to contract the actuator based on a received control signal. The actuators can comprise one or more cables operably coupled to a series of linkages configured to move axially between the chest wall and the nipple of the user.

In embodiments, an external device can be coupleable to the controller to provide operational parameters to configure the movement pattern. The external device can comprise a user interface configured to receive parameters from the user. The user interface can further be configured to display data received from one or more sensors to the user.

In embodiments, the storage compartment comprises a connection adapted to interface with an artificial nipple for feeding an infant.

In embodiments a method for collecting milk from a lactating breast can include warming mammary glands within the breast to a temperature between 35° Celsius and 42° Celsius, selectively applying pressure to a region of the breast by controlling a plurality of manipulable members operably coupled to actuators in an extraction mechanism and arrangeable circumferentially about the breast to move according to a movement pattern. The movement pattern can be configured to stimulate the breast to induce a flow of milk from the breast. The milk can be received in a storage compartment of a collection mechanism that is operably coupleable to the extraction mechanism proximate the nipple of the breast.

In embodiments, a method for collecting milk from a lactating breast can include receiving at a controller a threshold parameter based on a level of fullness of the breast, such as a strain threshold parameter, and receiving a signal indicative of a level of fullness of the breast provided by at least one sensor arranged proximate the breast. In response to detecting the level of fullness of the breast being above the threshold parameter the method can include automatically collecting the milk from the breast by: stimulating a flow of milk from the breast by applying heat to the breast extracting the milk from the breast by selectively applying mechanical pressure to a region of the breast by controlling a plurality of manipulable members operably coupled to actuators in an extraction mechanism and arrangeable circumferentially about the breast to move according to a movement pattern configured to induce a flow of milk from the breast. The flow of milk can be received in a storage compartment of a collection mechanism operably coupleable to the extraction mechanism proximate the nipple of the breast.

In embodiments the controller can determine if the collection mechanism is operably coupled to the extraction mechanism before collecting the milk from the breast. In embodiments, user approval can be requested before collecting milk from the breast.

In embodiments, the lactation system can comprise at least one extraction mechanism including a compression mechanism and a collection mechanism, and a controller. The compression mechanism can include a plurality of manipulable members, each operably coupled to an actuator and arrangeable circumferentially about a breast of a user such that each member can be actuated to selectively apply pressure to a region of the breast. The collection mechanism can be removably coupleable to the compression mechanism proximate the nipple of the user and comprise a storage compartment to receive and store a flow of milk from the breast. The lactation system can further include a wearable garment comprising an inner structure configured to be removably coupled to the at least one extraction mechanism and an outer cover comprising padding and arrangeable to conceal the at least one extraction mechanism.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures.

FIG. 8A is a perspective view depicting an actuator, according to an embodiment.

FIG. 8B is a perspective view depicting an actuator, according to an embodiment.

Figure 1A:
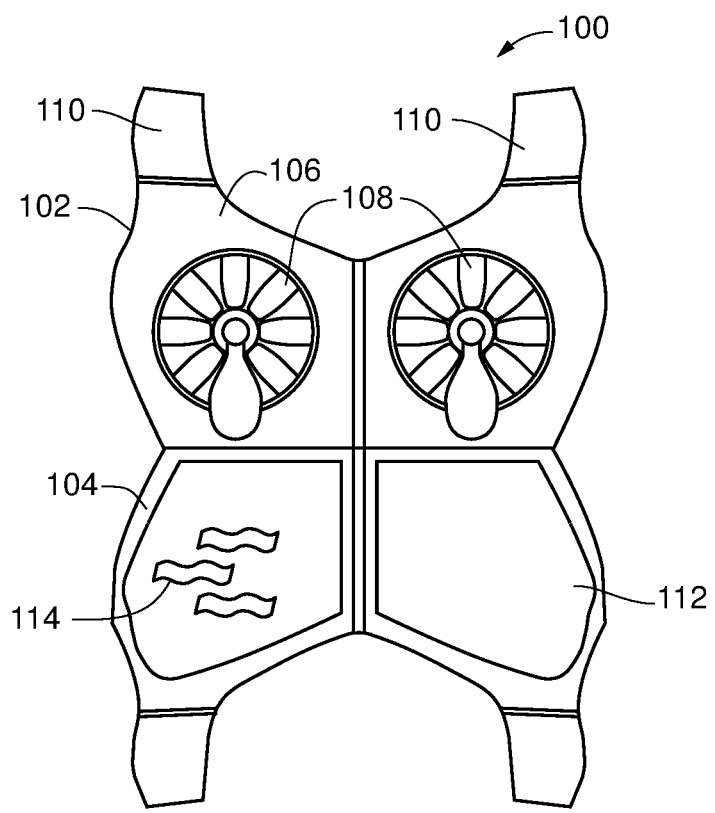
FIG. 1A is a plan view depicting a lactation system, according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Figure 1B:
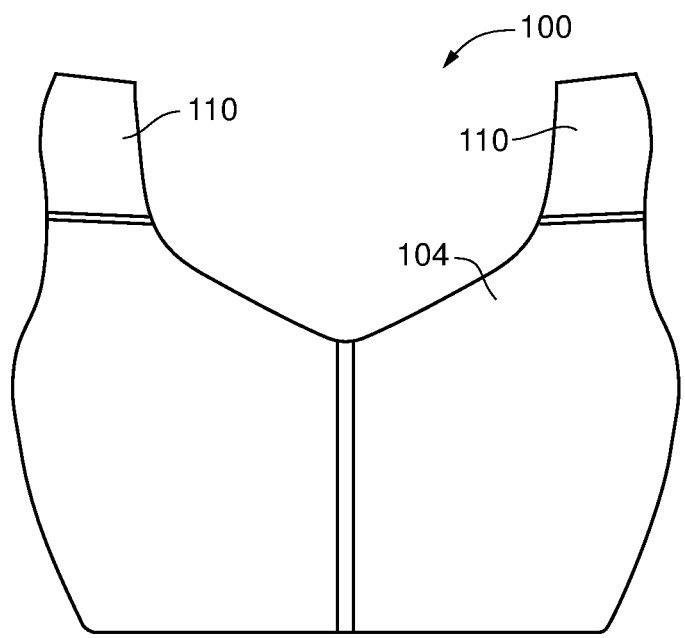
FIG. 1B is a plan view depicting a wearable garment, according to an embodiment.
Figure 1C:
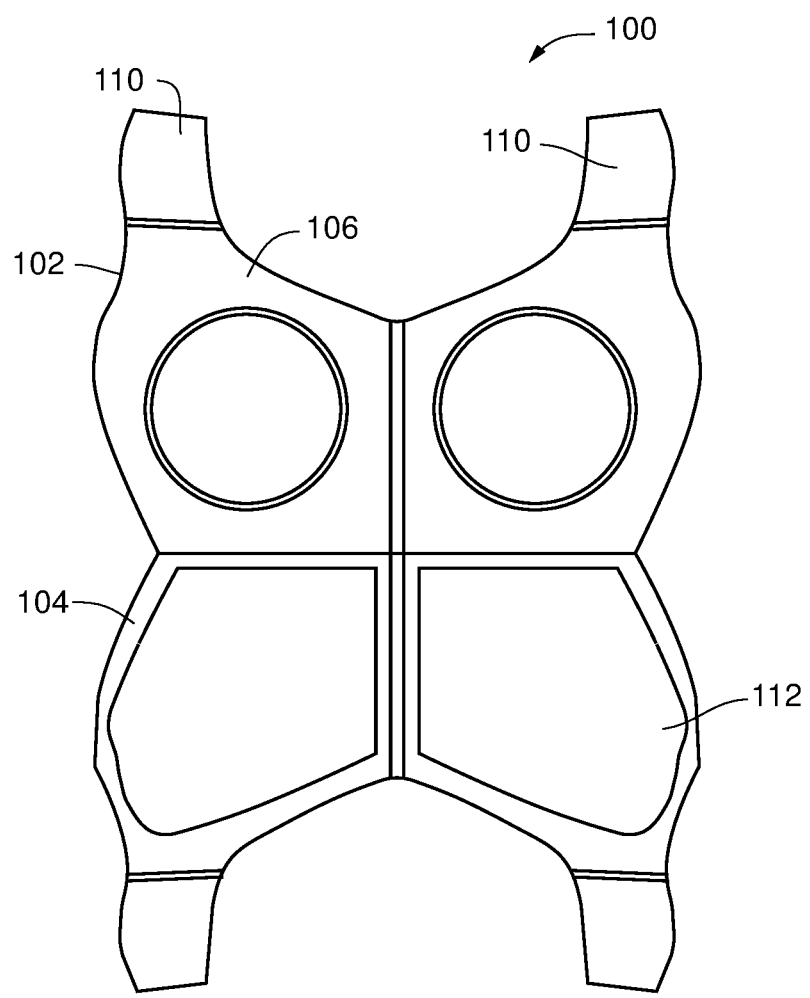
FIG. 1C is a plan view depicting a wearable garment, according to an embodiment.

FIGS. 1A-1C are plan views depicting a lactation system 100 according to an embodiment. FIG. 1A depicts an embodiment of a wearable garment 102 unfolded to reveal outer cover 104 and inner structure 106 that can receive one or more inserts 108. Each insert 108 can comprise extraction mechanism 200 and collection mechanism 300. Extraction mechanism 200 can further comprise compression mechanism 400. FIG. 1B depicts the wearable garment 102 of FIG. 1A with the outer cover 104 in place to conceal inserts, 108. FIG. 1C depicts wearable garment 102 with inserts 108 removed.

Wearable garment 102 can comprise a garment such as a brassiere, camisole, sling, or other form of garment adapted to be worn over at least a portion of the user's upper torso. Wearable garment 102 can comprise shoulder straps 110, and can include one or more closure mechanisms such as zippers, hook-and-eye closures, hook and loop fasteners or touch fasteners, buttons, or other closure mechanisms known in the art. Wearable garment 102 can further comprise padding 112, which can be removably or fixedly coupled to outer cover 104 or inner structure 106, in embodiments. Padding 112 can comprise sufficiently thick, conformable material to obscure inserts 108. The various components of wearable garment 102 can comprise fabric, or fabric like materials (such as leather or vinyl). In embodiments, some or all of wearable garment 102 can comprise stretchable materials such as knit fabrics, or materials comprising elastics, enabling wearable garment 102 to conform to the body of the user. While FIGS. 1A-1C depict a wearable garment including two inserts, embodiments of wearable garment 102 can be configured to receive a single insert.

System 100 can comprise a stimulation mechanism 114 to provide heat energy to the breast tissue to achieve a desirable temperature within the mammary glands for milk extraction. In embodiments, the desirable temperature can be between about 35° C. and about 42° C. Stimulation mechanism 114 can comprise one or more heating elements within wearable garment 102, such as within padding 112, or within insert 108. The stimulation mechanism 114 can comprise the wearable garment 102 itself, where the wearable garment 102 comprises materials or other features enabling capture of body heat from the user, or mechanically or electrically generated heat provided by various the mechanisms of insert 108, discussed below. Other heating methods or elements can also be used, including heating elements external to wearable garment 102 itself.

Figure 2A:
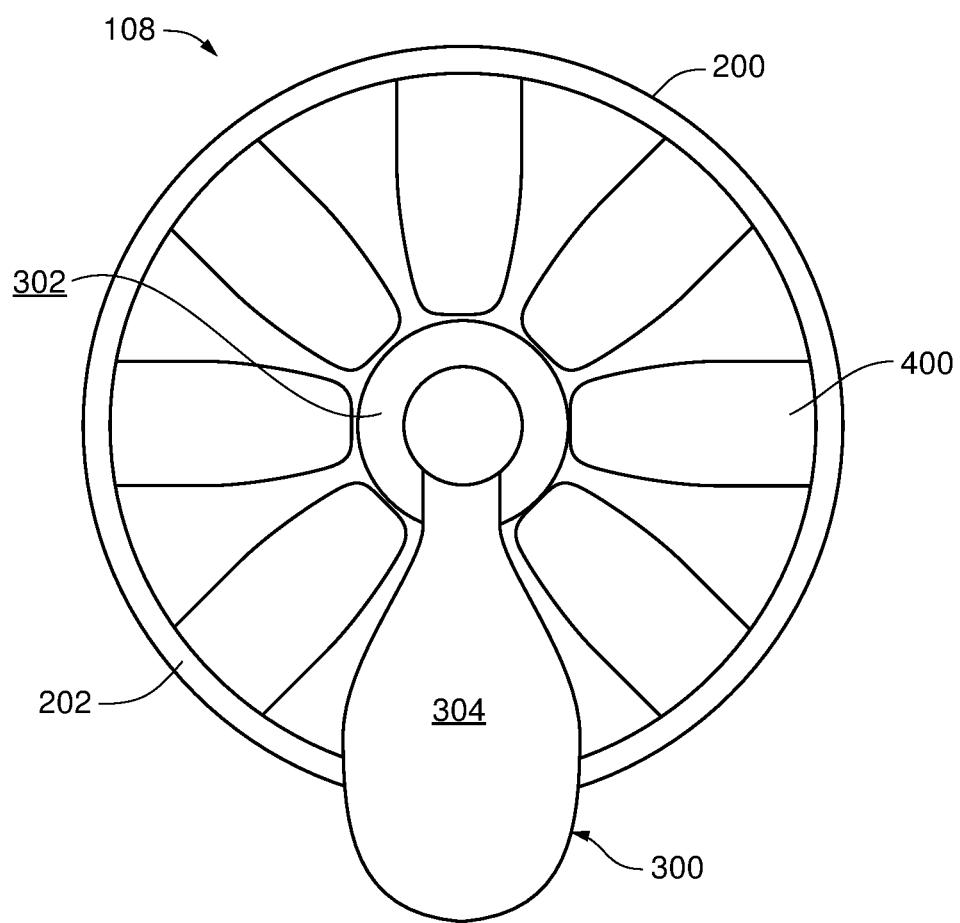
FIG. 2A is a plan view depicting an extraction mechanism, according to an embodiment.
Figure 2B:
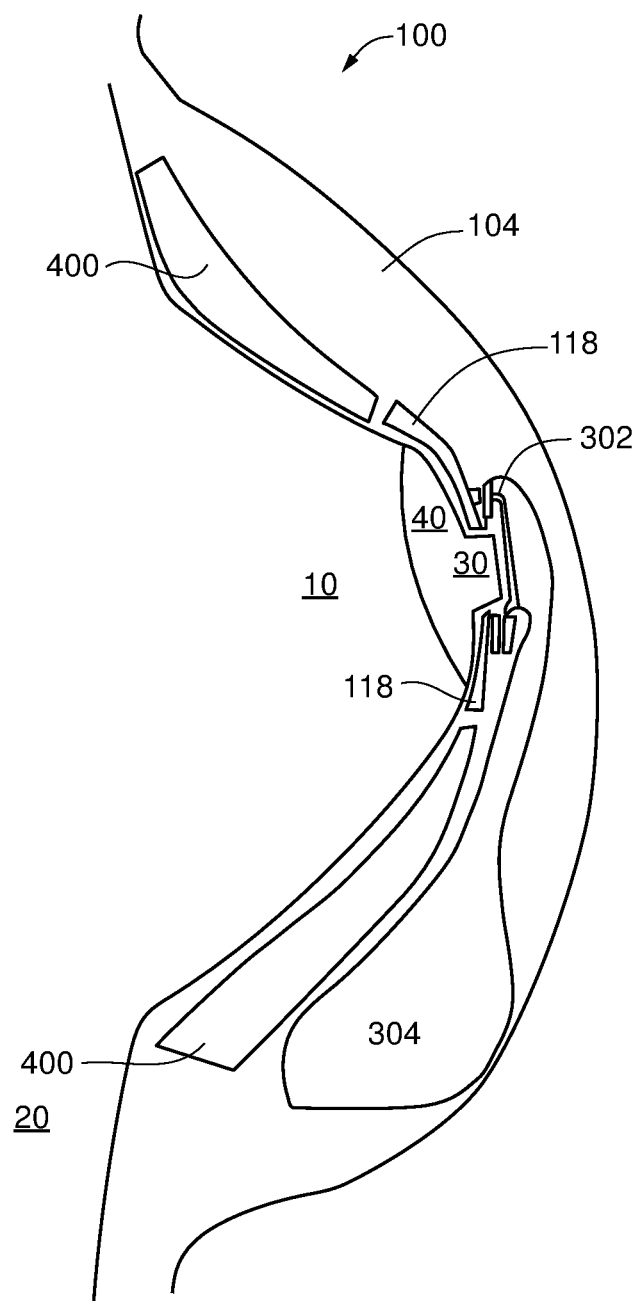
FIG. 2B is a partial cross-sectional view depicting a lactation system, according to an embodiment.

FIG. 2A is an anterior view depicting an embodiment of an insert 108. Extraction mechanism 200 can comprise tissue stabilization mechanism 202 which can be arranged proximate the chest wall 20 of the user. Tissue stabilization mechanism 202 can provide static compression to the breast tissue to assist in the milk extraction process and to provide support and comfort to the user. FIG. 2B is a partial cross-sectional view of an insert 108, according to an embodiment as fitted over the breast 10 of the user.

Figure 3:
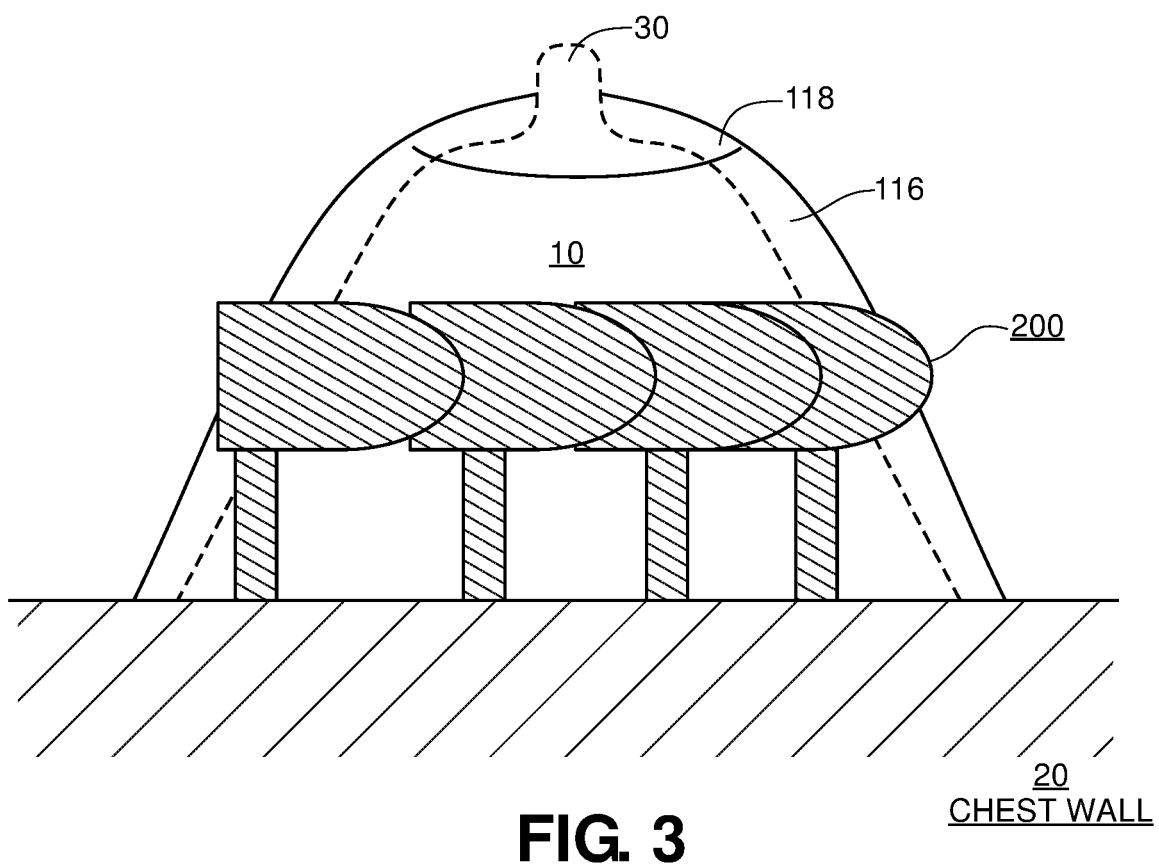
FIG. 3 is a plan view depicting an insert, according to an embodiment.

In embodiments, all or part of insert 108 can be arrangeable within wearable garment 102 such that the various components of insert 108 are separated from the skin of the wearer. For example, wearable garment 102 can comprise a mesh or fabric layer which can rest between insert 108 and the user. In addition and/or in the alternative, insert 108 can further comprise an insert cover 116, as depicted in FIG. 3, configured to separate extraction mechanism 200 from the user. Insert cover 116 can further comprise a collection interface 118 for attachment to collection mechanism 300. Insert cover can be rigid to provide additional support, in embodiments, or flexible to enable conformation with body curvature.

Collection mechanism 300 can be arranged proximate the nipple 30 and be removably affixed to insert 108 via collection interface 118. Collection mechanism 300 can comprise connection 302, and storage compartment 304. Storage compartment 304 can comprise a pouch, sac, bottle, or other collection receptacle for collecting expressed breast milk. Storage compartment 304 can comprise a sterilizable material (such as latex or silicone rubber). Connection 302 can be configured to engage with a cover, and/or a teat (artificial nipple) and associated fixation device to enable the feeding of an infant from the storage compartment 304. Connection 302 can therefore present threads, or other mechanism for attachment to interface 118.

Figure 4A:
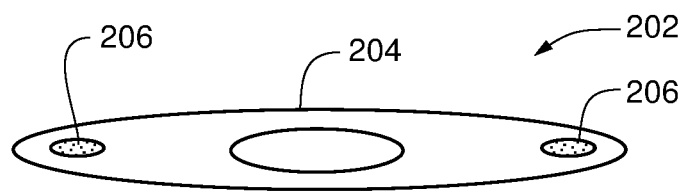
FIG. 4A is a plan view depicting a tissue stabilization mechanism, according to an embodiment.
Figure 4B:
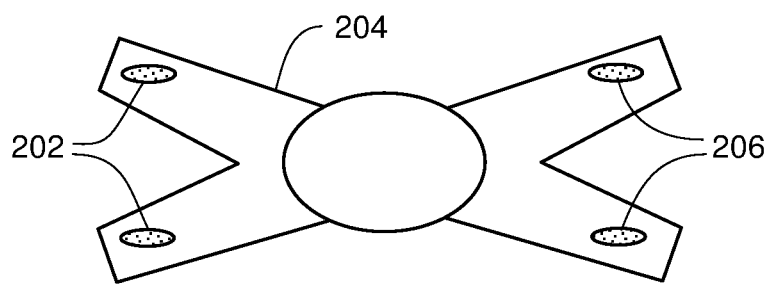
FIG. 4B is a plan view depicting a tissue stabilization mechanism, according to an embodiment.
Figure 4C:
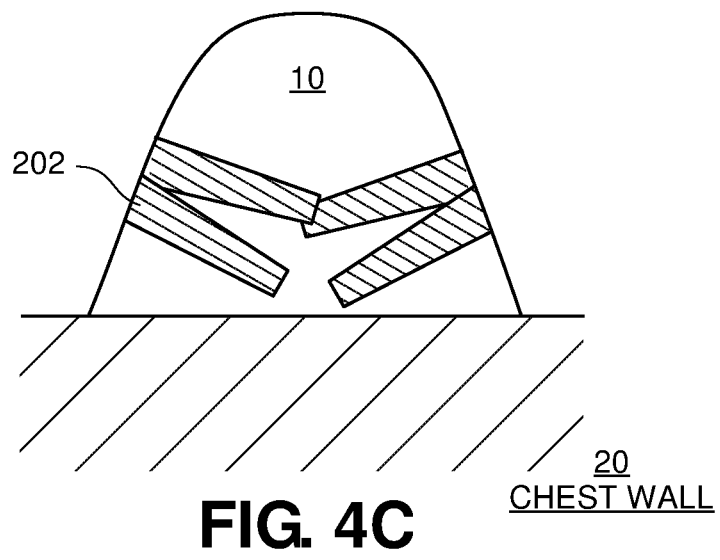
FIG. 4C is a plan view depicting a tissue stabilization mechanism, according to an embodiment.

FIGS. 4A-4F depict various embodiments of a tissue stabilization mechanism 202 that can be arranged circumferentially about the breast 10 of the user. Tissue stabilization mechanism 202 can comprise one or more features to enable removable fixation of insert 108 within wearable garment 102. As can be seen in FIGS. 4A and 4B, tissue stabilization mechanism 202 can comprise an elongate body 204, and one or more securement mechanisms 206. Body 204 can comprise a multi-layered material to provide rigidity and reduce the degrees of freedom of the breast tissue proximate the chest wall 20 during active compression as provided by compression mechanism 400 (discussed in more detail below). Securement mechanisms 206 can comprise buttons, hook-and-loop closures, tabs, slots, or other features enabling opposite ends of the body 204 to be joined, removably fixing tissue stabilization mechanism 202 to the breast 10 of the user. In embodiments, securement mechanism 206 can be adjustable, enabling varied morphology, fits, and assembly/disassembly of wearable garment 102 and insert 108. FIG. 4C is a side view depicting an embodiment of the tissue stabilization mechanism arranged around the breast 10 of a user, proximate the chest wall 20.

Figure 4D:
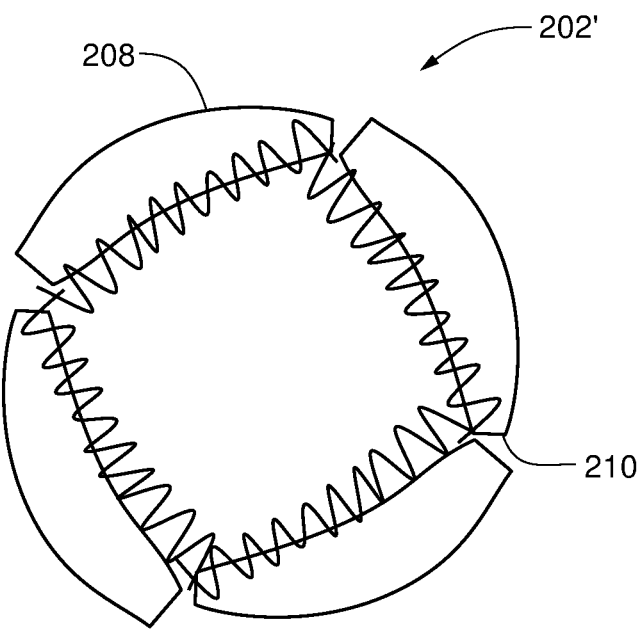
FIG. 4D is a plan view depicting a tissue stabilization mechanism, according to an embodiment.
Figure 4E:
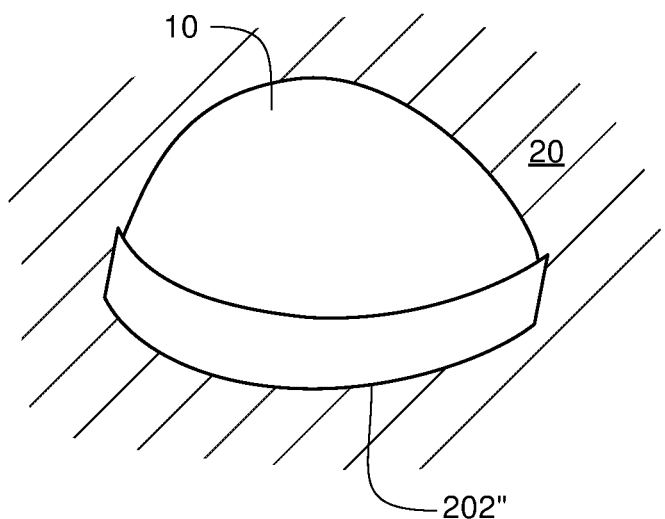
FIG. 4E is a perspective view depicting a tissue stabilization mechanism, according to an embodiment.
Figure 4F:
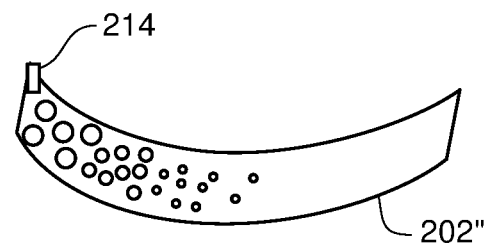
FIG. 4F is a perspective view depicting a tissue stabilization mechanism, according to an embodiment.

FIG. 4D is an anterior view depicting an alternative embodiment of a tissue stabilization mechanism 202'. Tissue stabilization mechanism 202' can comprise a plurality of plates 208, that can be joined with elastic or spring members 210 for arrangement about the breast of the user. Spring members 210 can draw plates 208 radially inward, providing a static compress ion of the breast tissue proximate the chest wall 20. FIGS. 4E and 4F are perspective views of yet another embodiment of tissue stabilization mechanism 202". Tissue stabilization mechanism 202" can comprise a one-way valve 214 enabling air to escape when opened. This can result in a slight pressure to create a firm fit around the breast tissue.

Figure 5A:
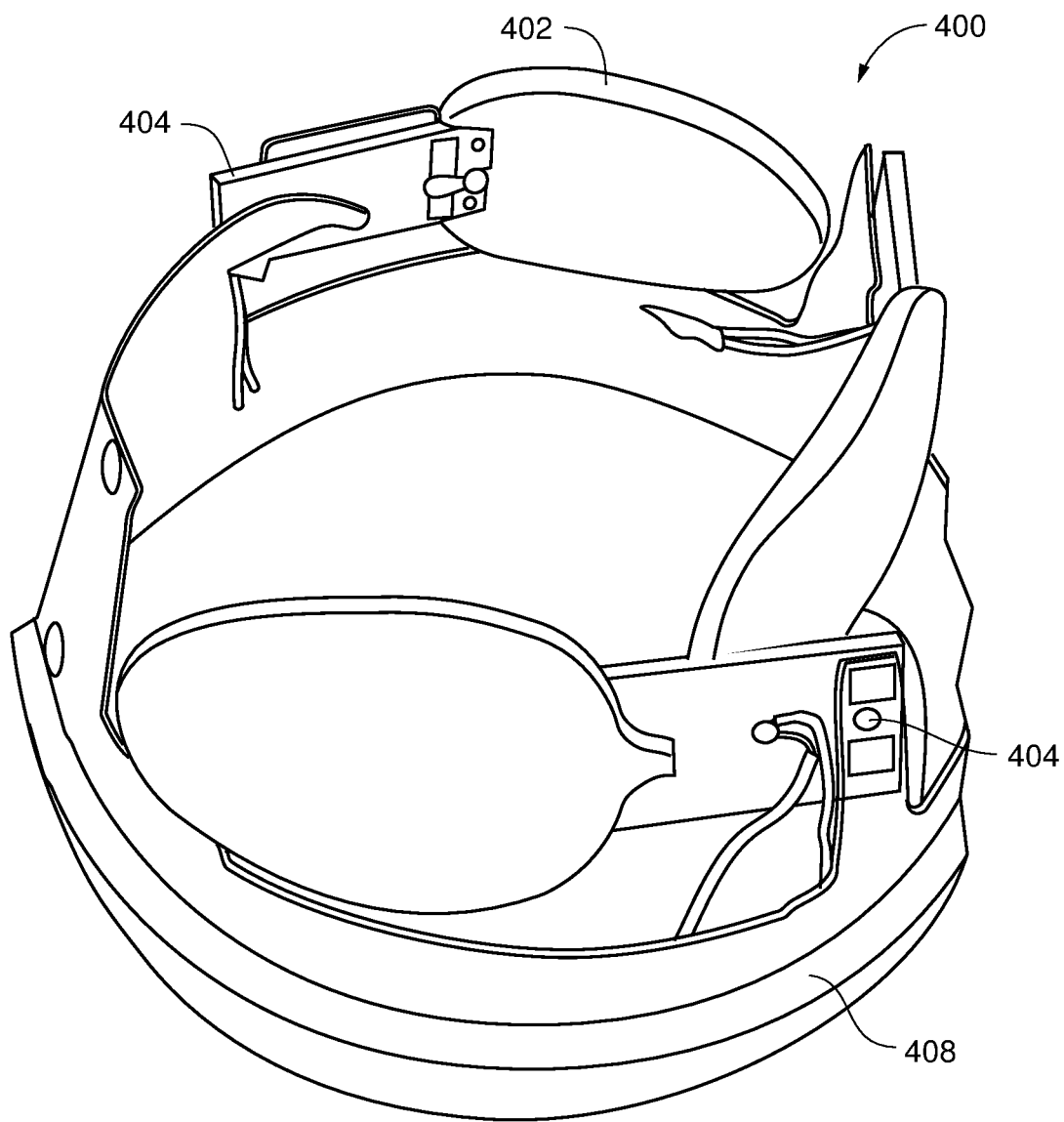
FIG. 5A is a perspective view depicting a compression mechanism, according to an embodiment.
Figure 5B:
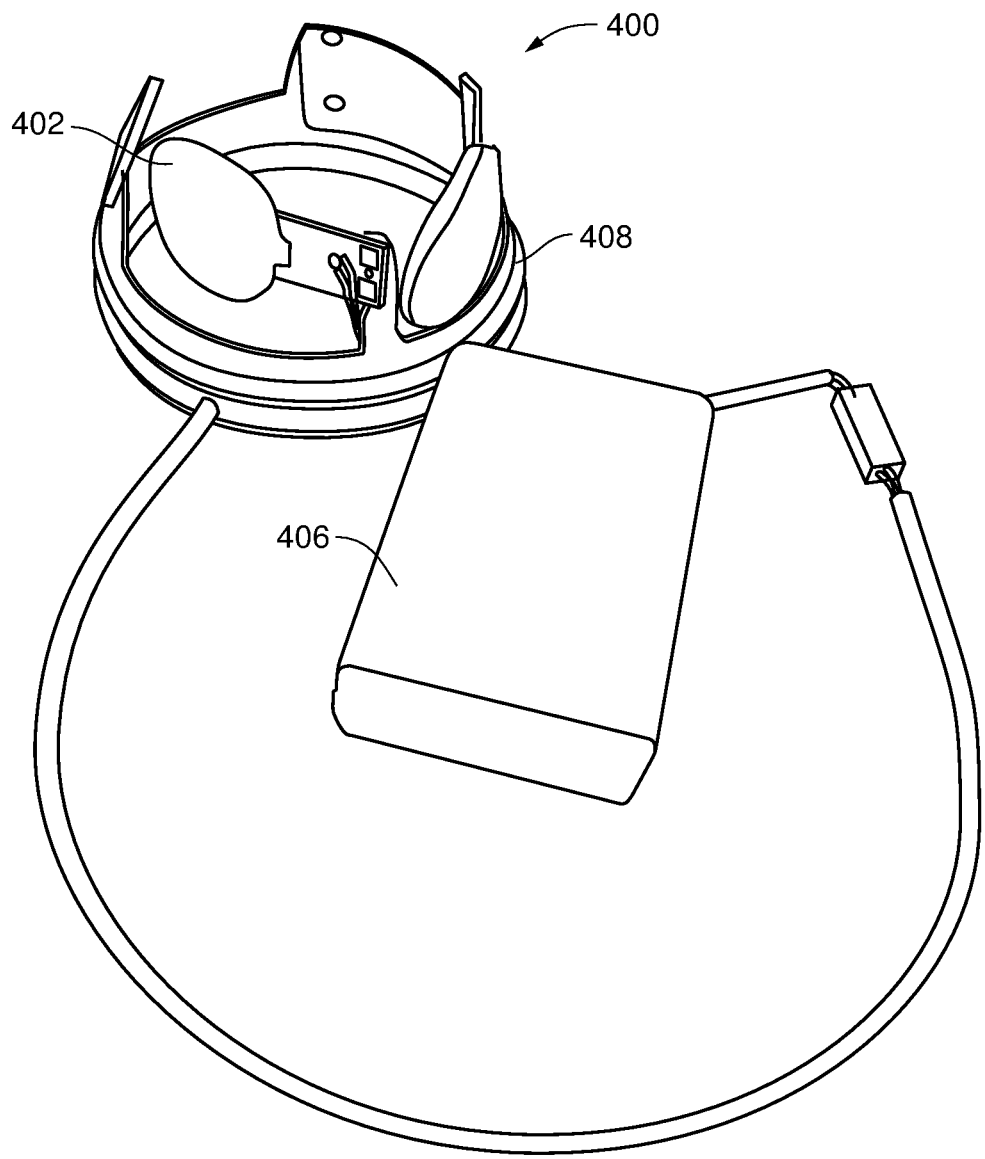
FIG. 5B is a perspective view depicting a compression mechanism, according to an embodiment.

FIGS. 5A and 5B are perspective views depicting an embodiment of a compression mechanism 400. Compression mechanism 400 can be arranged around the breast 10 of the user, posterior to the nipple-areolar complex 40. Compression mechanism 400 can comprise a plurality of manipulable members 402, operably coupled to one or more actuators 404. Actuators 404 can be electrically coupleable to, and powerable by a power supply 406 and/or a control system 500.

Power supply 406 can be a direct-current power supply. Power supply 406 can comprise a battery housing configured to receive one or more alkaline or rechargeable battery cells. Power supply 406 can further comprise piezoelectric, solar, thermal, or other energy capture mechanisms configured to charge battery cells or to directly power actuators 404. In embodiments, power supply 406 can be coupleable to wearable garment 102, or external to the other components of system 100. In embodiments, power supply 406 can comprise a contoured housing adapted for comfortable arrangement on or near the body of the user. Those of ordinary skill in the art will appreciate that power supply 406 can comprise any format or mechanisms capable of providing power to actuators 404 to move members 402.

Figure 6:
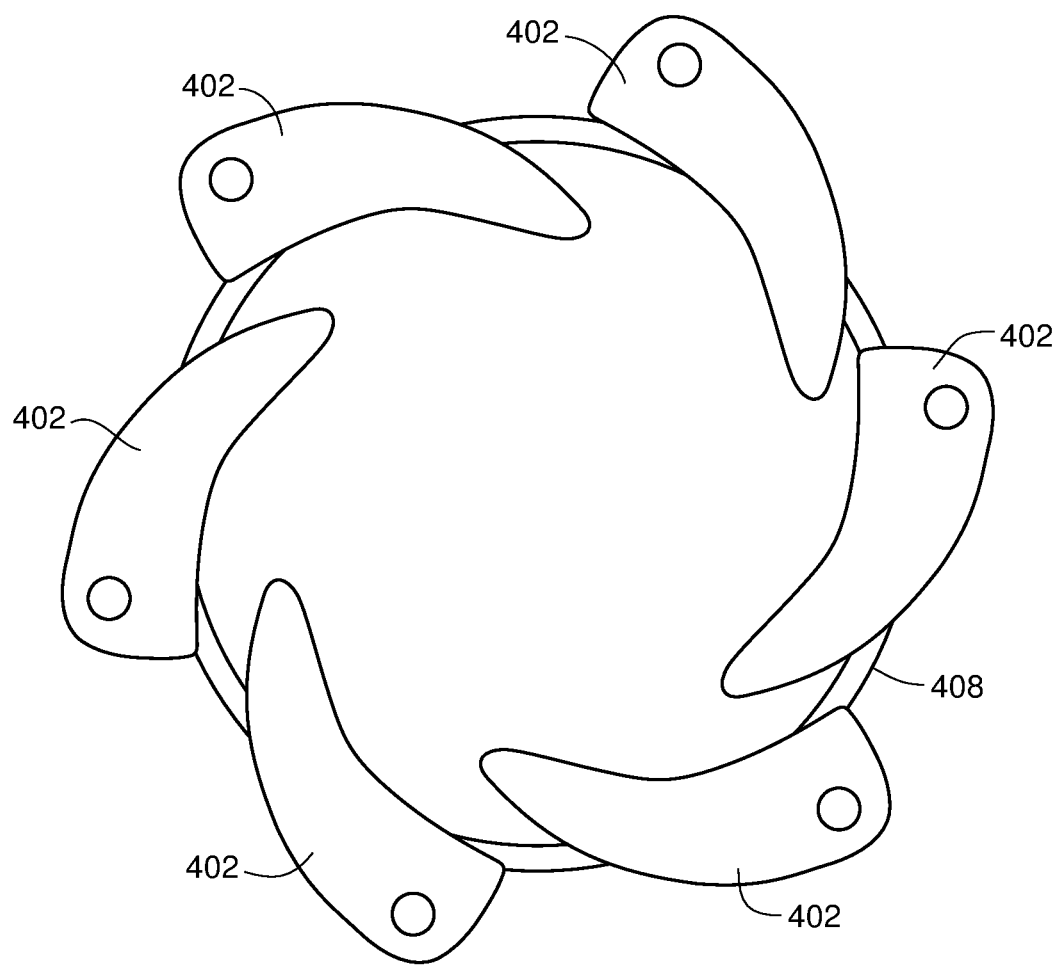
FIG. 6 is a plan view depicting a compression mechanism, according to an embodiment.

As can be seen in FIG. 6, members 402 can be radially spaced such that when compression mechanism 400 is arranged proximate the nipple-areolar complex 40, the members can contact the tissues laterally, medially, superiorly, and inferiorly. The quantity of members can vary in embodiments based on the size of the members 402 and the size requirements for compression mechanism 400. Members 402 can be positioned proximate the chest wall, and extend toward, but not reach, the nipple-areolar complex 40. In embodiments, static ring 408 can comprise part or all of tissue stabilization mechanism 202. In embodiments, the number of members 402 can also be customized by the user. Members 402, with or without corresponding actuators 404 can be removably coupled to a static ring 408, such that members of different sizes, shapes and/or materials can be chosen to provide a preferred fit or action for the user. For example, members 402 that are arranged in lateral, medial and inferior positions can be longer than members 402 in an arranged superiorly to the breast 10.

Figure 7A:
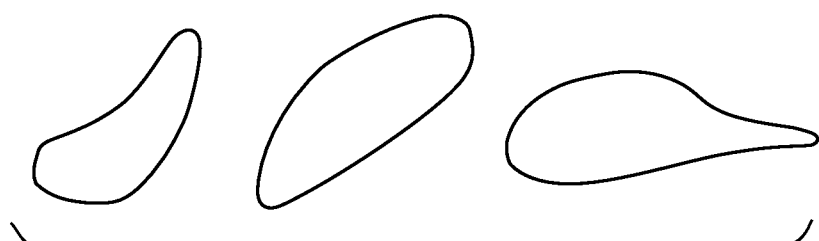
FIG. 7A is a perspective view depicting embodiments of members.
Figure 7B:
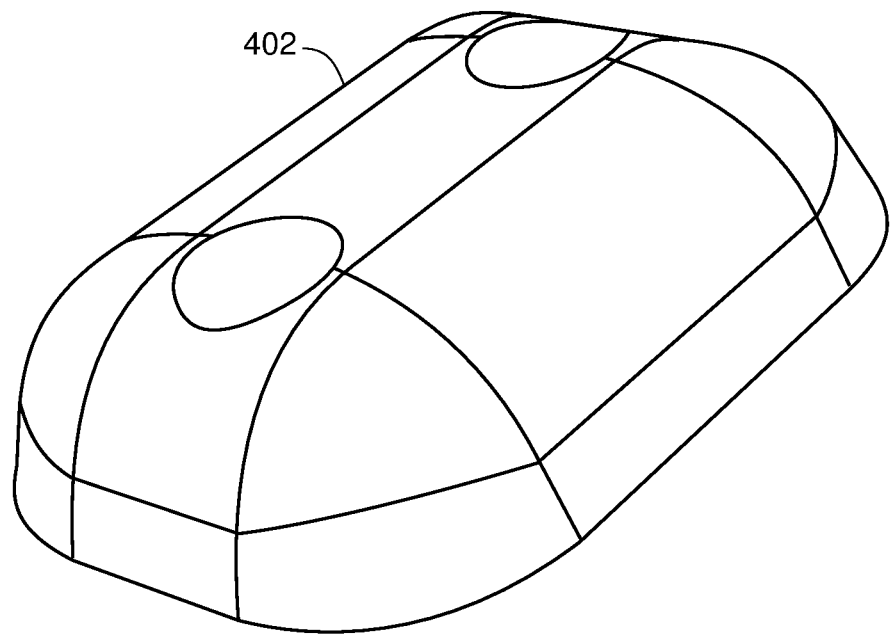
FIG. 7B is a perspective view depicting a manipulable member, according to an embodiment.
Figure 7C:
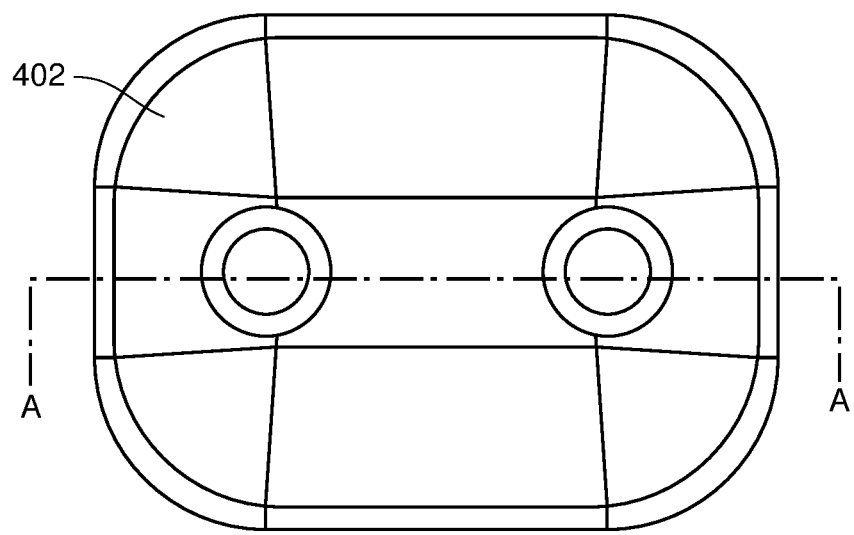
FIG. 7C is a top view depicting a manipulable member, according to an embodiment.
Figure 7D:
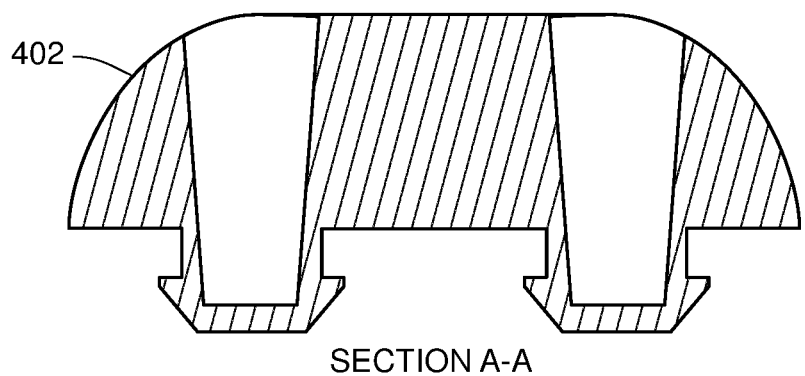
FIG. 7D is cross-sectional view depicting a manipulable member, according to an embodiment.
Figure 7E:
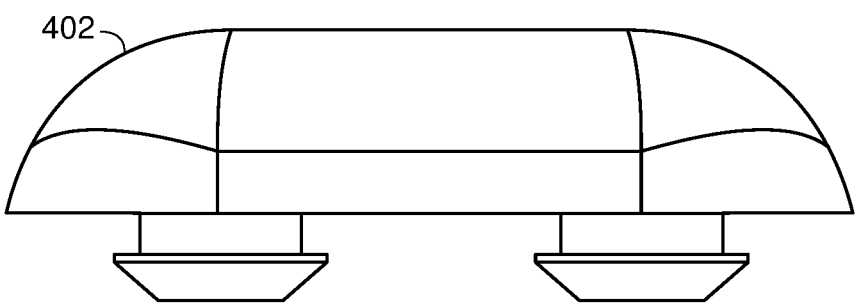
FIG. 7E is a plan view depicting a manipulable member, according to an embodiment.

Each member 402 can comprise a generally petal or spoon-shaped form, adapted to enable a concave surface of the member 402 to conform to the concave surface of the breast 10 of the user. FIG. 7A depicts a variety of embodiments of members 402 that can conform to different sizes and configurations of body curvature. FIGS. 7B-E are plan and perspective views depicting a member 402, according to an embodiment. The angle of take-off or curvature of the members 402 can be determined based on actual breast geometry. For example, members 402 can be custom fitted for a user based on measurements taken from the individual user, for example by direct measurement, or 2/3D dimensional imaging technology. Members 402 can comprise rigid, flexible, or conformable materials such as plastic, silicone, urethane, or materials. The various embodiments of compression mechanism 400 depicted herein provide further examples of members 402 that can be used.

FIGS. 8A and 8B are perspective views depicting embodiments of a member 402 and actuator 404. FIG. 8A depicts actuator 404 in a neutral state, FIG. 8B depicts actuator 404 in a contracted state. Actuators 404 can comprise shape-memory alloy (SMA) actuators, servos, cable-driven linkages, or other mechanisms enabling members 402 to move in a cyclic fashion to provide active compression of the breast tissue. Actuators 404 can comprise one or more cables 410, which can be SMA wires. Where cables 410 comprise shape-memory materials, cables 410 can vary in length in response to an electrical current, resulting in contraction of actuator 404, and radially inward movement and rotation of member 402. Other methods of contracting actuator 404 can be used. For example, cables 410 can be at least partially wound to a bobbin or spindle, which can be rotated to shorten or lengthen cable 410 as required. Actuator 404 can further comprise a plurality of stabilization plates 412. In embodiments, actuators 404 can provide mechanical compressive pressure to the breast tissue between about 0 mmHg and 215 mmHg, with an average between about 25 mmHg and 40 mmHg. The mechanical compressive pressure can be applied circumferentially (around the tissue), radially (pushing inward toward the tissue, or a combination).

Figure 9:
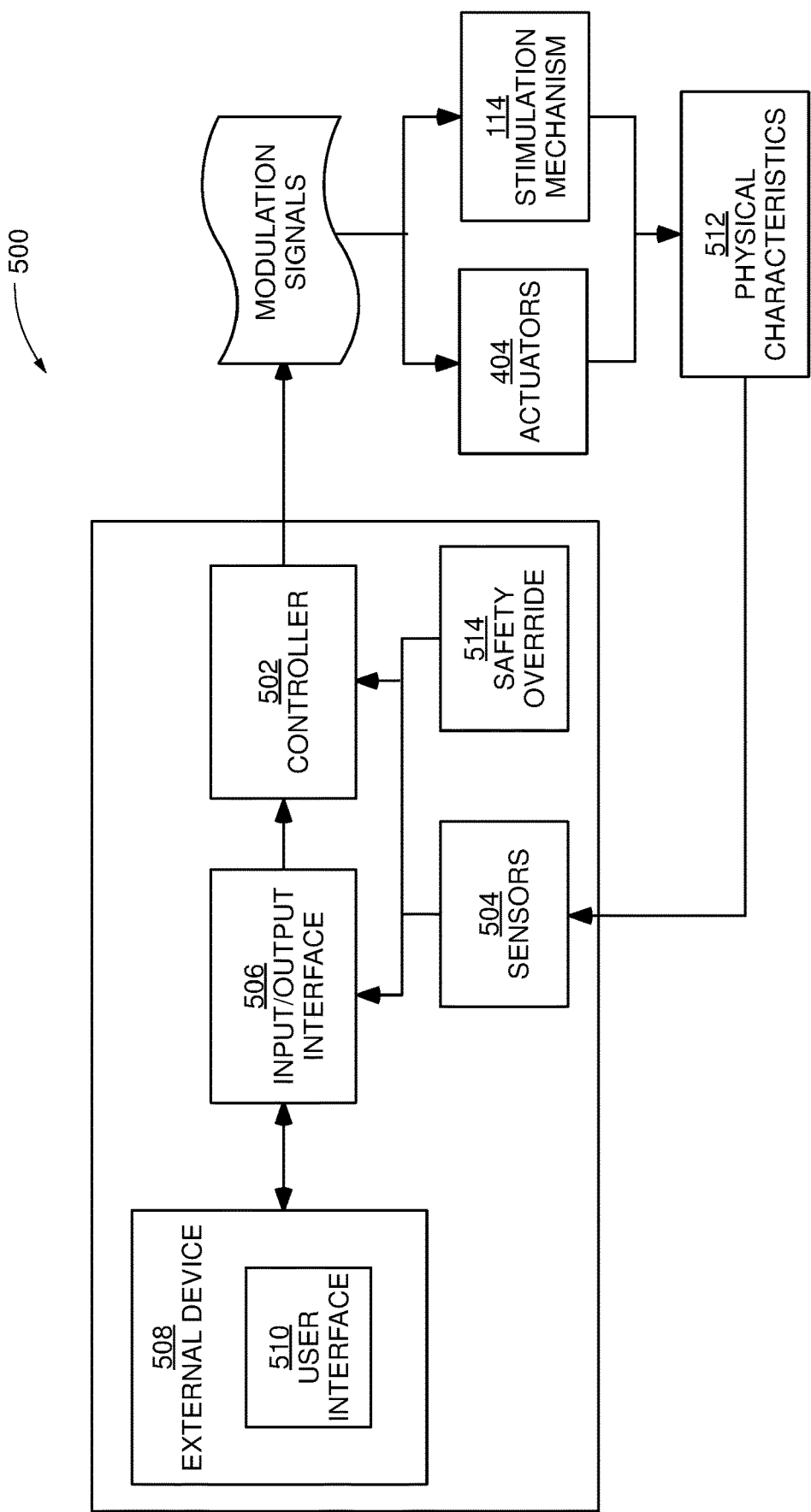
FIG. 9 is a schematic diagram depicting a control system, according to an embodiment.

Actuators 404 can be electrically coupled to a control system 500, an embodiment of which is depicted in FIG. 9. Control system 500 can comprise a controller 502, one or more sensors 504, and input/output interface 506. Controller 502 can be configured to modulate an electrical current or other signal in order to induce actuators 404 to move members 402 in one or more patterns adapted to induce the expression of breast milk through mechanical compression of the breast tissue. Controller 502 can also provide modulation signals to stimulation mechanism 114 to produce heat. In embodiments, each actuator 404 can receive a separate signal from controller 502, enabling individual actuator control. In other embodiments, all actuators 404 can be modulated with a single signal, or groups (such as opposing pairs) of actuators 404 can be modulated together. Actuators 404 can be water-proof or water-resistant, in embodiments. For example, actuators 404 can comprise waterproof components, or can be treated with a flexible waterproofing finish material.

Input/output interface 506 can comprise a wired or wireless interface for communication with an external device 508 such as a computer system, tablet, smart phone, mobile device, or the like. External device 508 can comprise user interface 510. User interface 510 can receive user inputs including control parameters and provide user outputs regarding configuration and status of lactation system 100, such as sensor data. User interface 510 can comprise a mobile application, web-based application, or any other executable application framework. User interface 510 can reside on, be presented on, or be accessed by any computing devices capable of communicating with input/output interface 506, receiving user input, and presenting output to the user.

Actuators 404 and stimulation mechanism 114 can modify various physical characteristics 512 detectable by sensors 504. Sensors 504 can comprise one or more temperature sensors to detect the temperature within and around lactation system 100. Sensors 504 can comprise one or more pressure sensors to detect an actual amount of force being applied to the breast tissue by members 402. Sensors 504 can comprise strain sensors to detect force applied to the members 402 by the breast tissue. In embodiments, actuators 404 can provide strain, pressure, or other data. Sensors 504 can comprise one or more accelerometers to detect the movement of members 402, or the movement, posture, or other characteristic of the user. Sensors 504 can comprise one or more flow meters, volume sensors, or weight sensors to detect the amount of milk flowing into, or stored within, collection mechanism 300. Control system can further comprise a safety override 514 to enforce one or more safety limitations such that members 402 will not be induced to move in a manner that is potentially harmful to the user.

Figure 10A:
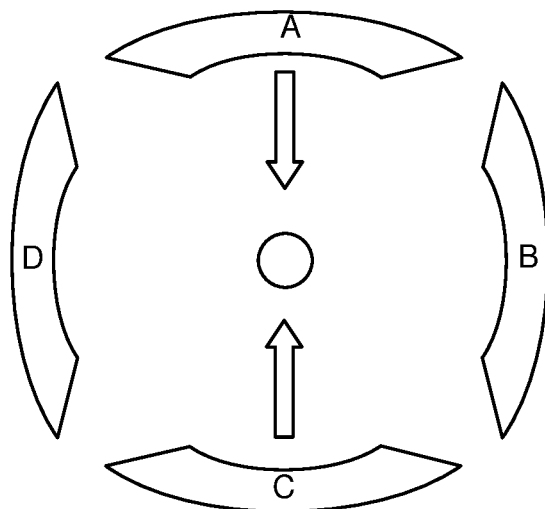
FIG. 10A is a schematic diagram depicting a movement pattern, according to an embodiment.
Figure 10B:
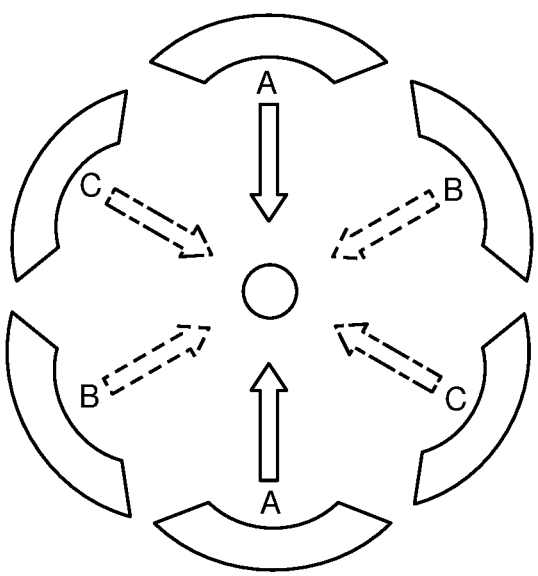
FIG. 10B is a schematic diagram depicting a movement pattern, according to an embodiment.

Based on input parameters and sensor data, control system 500 can control the position and movement of members 402 according to a variety of different patterns to induce the flow of breast milk. In one embodiment, depicted schematically in FIG. 10A, members 502 can be controlled such that opposing pairs (or groups) of members are induced to provide mechanical compression in synchronized pairs. For example, A and C can compress inward, while B and D remain fixed. The alternating pattern of compressing and fixed members 402 can enhance the compressive force by limiting the ability of the breast tissue to be moved away from the compressing members 402. FIG. 10B depicts another embodiment of a movement pattern using six members 402, the pair of members labeled A can be moved first, followed by B, and C. Control system 500 can further control members to produce a cyclic flattening and lengthening of the nipple 30 of the user, which can be in a manner tailored to mimic the behavior of a suckling infant.

Figure 11:
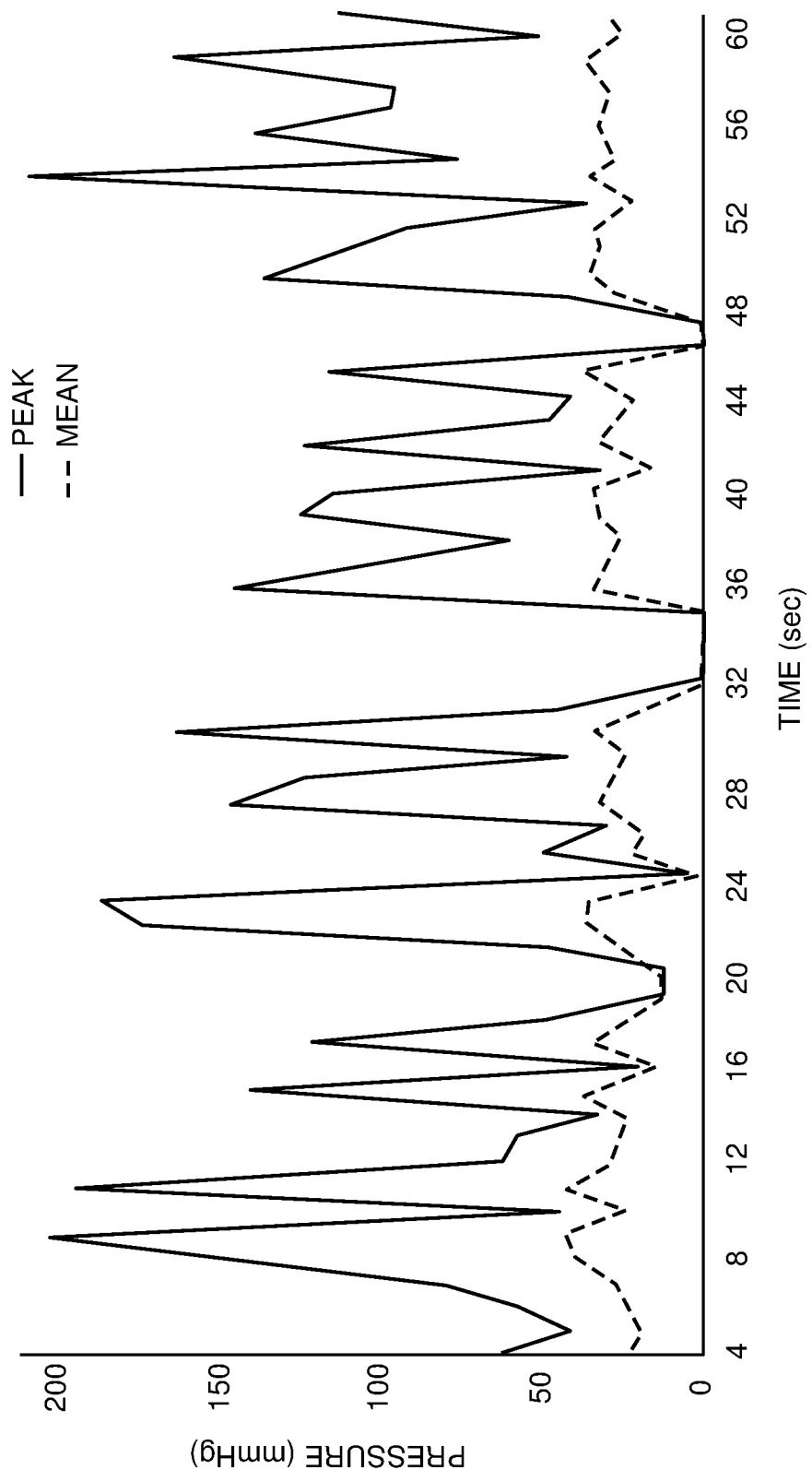
FIG. 11 is a graph depicting pressure levels of a movement pattern, according to an embodiment.

Other patterns of movement can be produced. For example, in one embodiment, compression can be effected using a burst pattern, including at least two peaks in compression, though other numbers of peaks can be used, for example, five or more. The peaks in compression can occur about every two to four seconds and have a duration of less than about one second. In embodiments, the burst patterns can occur every three to seven seconds. The burst pattern can include cycling through individual members 402 or pairs of members, such that a first set of members, can perform two or more peaks, and after a break period (of about three seconds), a second set of members, can perform two or more peaks, and so forth. The pressure applied during peaks can be up to about 200 mmHg, though other values can be used, for example about 40 mmHg. The pressure applied between peaks can be 0 mmHg, or another value such as around 20 mmHg. FIG. 11 is a graph depicting peak and mean pressures that can be applied, in embodiments. The burst pattern consisting of periods of high and low pressure can enable the beneficial retrograde flow of milk within the breast tissue.

The patterns and force of compression can be modified based on input parameters received through user interface 510. For example, user interface 510 can enable the user to assign one or more members 402 to activation groups (the members of which can be moved synchronously). The user interface 510 can receive parameters indicating the number of peaks per cycle, an upper pressure target, a minimum pressure target (to be used between peaks, or when the activation group is not moving), a duration of the peaks, a time period between peaks, and the order in which each activation group is to be used.

Control system 500 can further use the data from sensors 504 to determine optimal levels and locations of compressive force to use in order to maximize the amount and speed of milk extraction. For example, control system 500 can identify an area of a breast 10 that, when compressed, results in increased milk flow. The movement pattern can then be modified to provide more focus on that area. In another example, control system 500 may identify an area of a breast 10 (or even which of the user's breasts) has the most potential for milk extraction in order to direct the compressive force. In one embodiment, control system 500 can automatically begin extraction at specified times, or when the physical characteristics indicate that extraction would be appropriate. For example, it may be desirable to only extract milk when the user is at least partially upright, but is not in motion (i.e., sitting or standing still). The control system 500 can also verify that collection mechanism 300 is appropriately connected and that storage compartment 304 is has available storage capacity before beginning. Milk extraction can therefore be performed automatically without intervention by the user. Milk extraction sessions can be about twenty minutes in duration, though longer and shorter time periods can be used. The duration of each extraction session can be determined by an input parameter, or modified based on sensed milk extraction.

Figure 12:
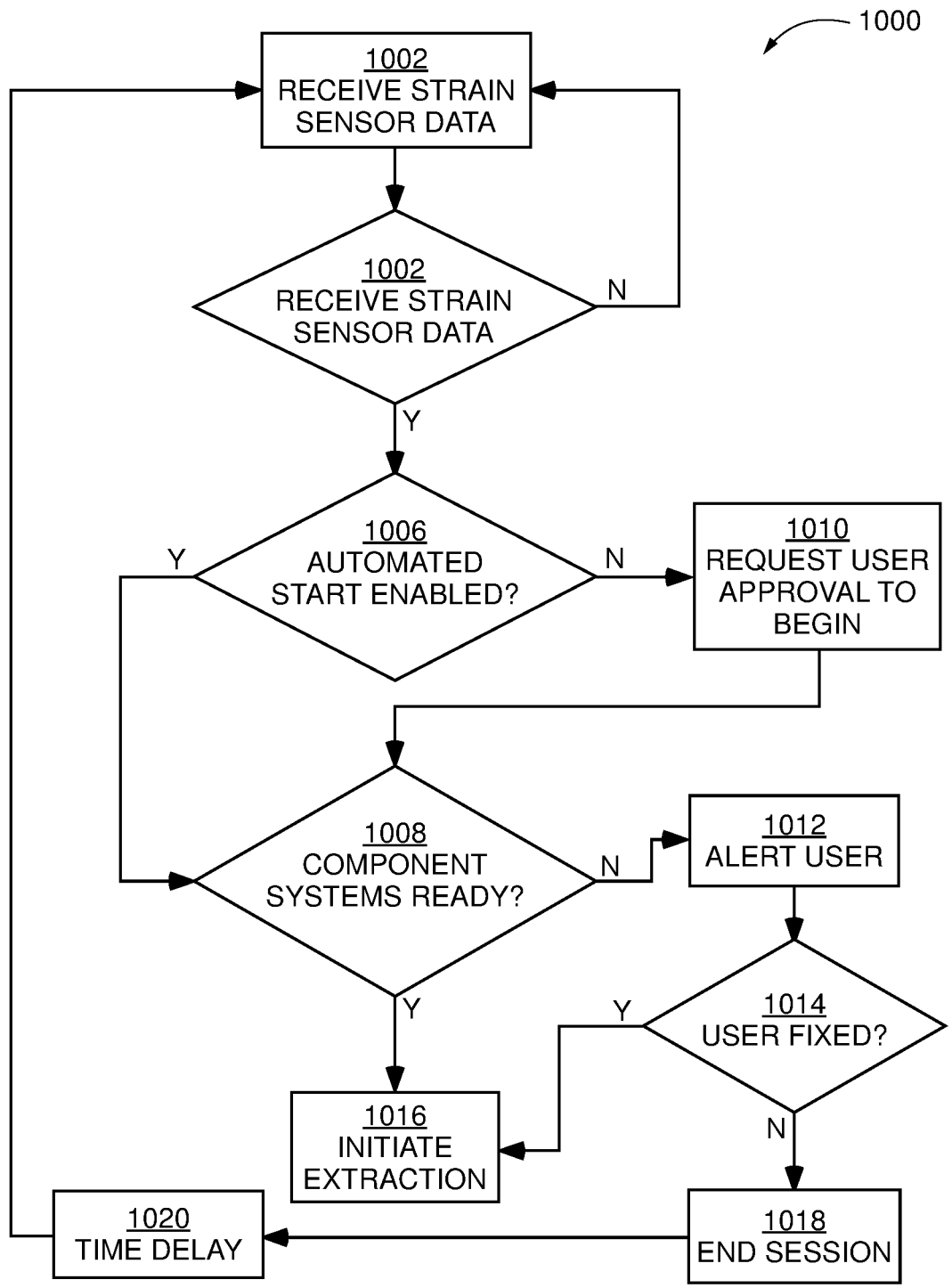
FIG. 12 is a flowchart depicting a method of initiation extraction, according to an embodiment.

FIG. 12 is a flowchart depicting a method 1000 for automatically beginning milk extraction, according to an embodiment. At 1002, strain data can be received from sensors 504. The strain can be checked against a threshold at 1004. The threshold can be a static threshold, or configurable by the user. In addition, different strain thresholds can be maintained for different areas of the breast, based on the location of strain sensors. Strain sensor data can therefore be used to determine that milk extraction is appropriate. If, at 1004, the strain is not above the threshold, control can iterate back to 1002 to monitor the strain sensor data. If the strain is detected to be above the threshold, and automated start is enabled (for example, via a user configuration setting), the components of lactation system 100 can be checked for readiness at 1008. If automated start is not enabled, a request can be made to the user for approval to initiate extraction at 1010. The user can be alerted to the request via external device 508. In embodiments, one or more components of insert 108 can be configured with hardware enabling it to beep, vibrate, light up, or provide other feedback to the user.

At 1008, the various components of system 100 can be checked to verify that the system is capable of safely extracting milk. For example, one or more sensors 504 can detect that collection mechanism 300 is correctly engaged and has available storage capacity. If the components are not ready, the user can be alerted at 1012. At 1014, if the user successfully remedies the problem, extraction can being at 1016. If, at 1008, all component systems are ready, control can proceed directly to 1016.

At 1014, if the user does not successfully remedy the problem (for example, if the user cancels the request, or a maximum time is reached), the current session can end at 1018, and control can return to 1002 to detect strain levels after a time delay at 1020.

Figure 13:
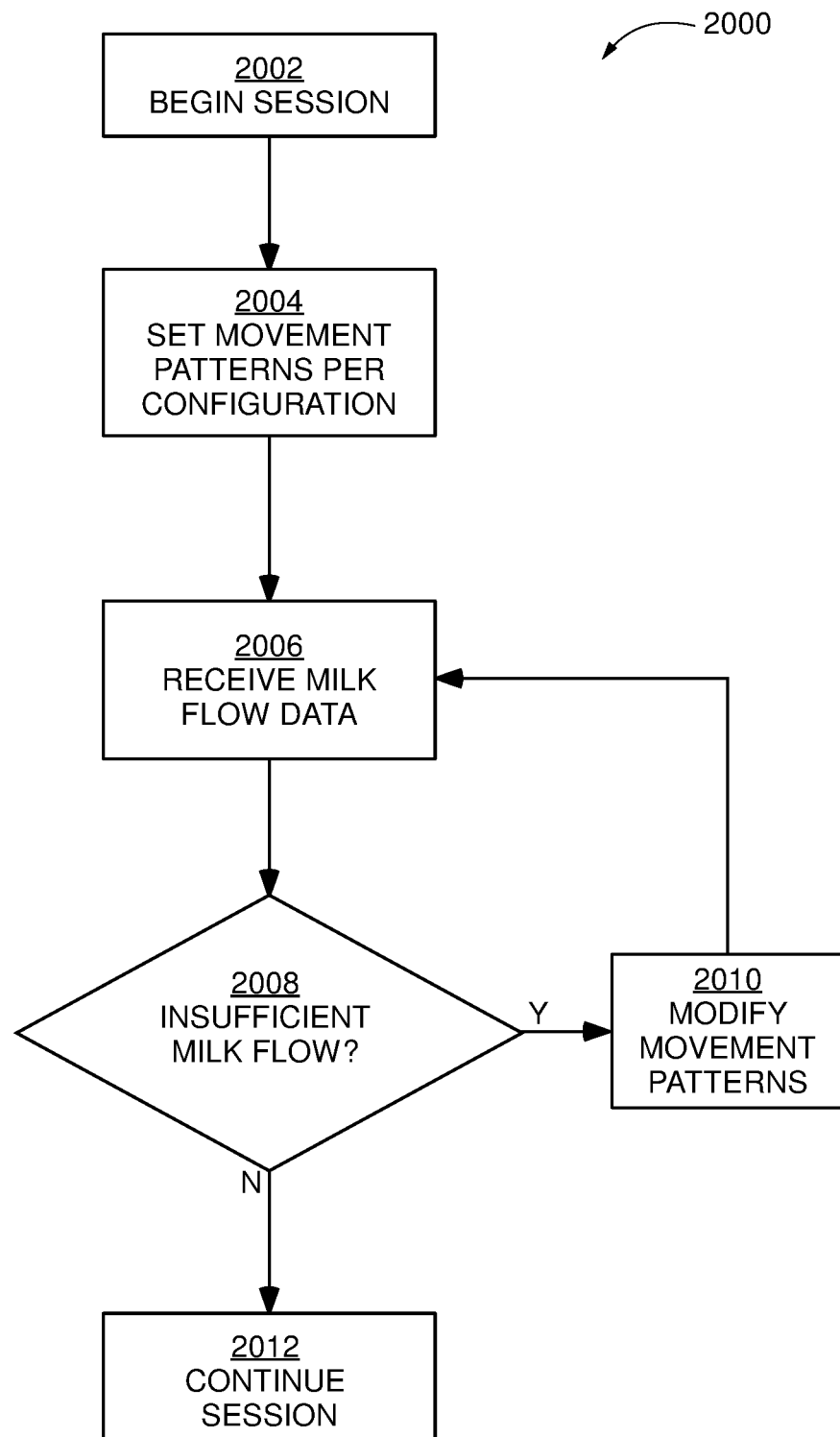
FIG. 13 is a flowchart depicting a method of initiation extraction, according to an embodiment.

FIG. 13 is a flowchart depicting a method 2000 for controlling a milk extraction session, according to an embodiment. At 2002, a session can begin. The session can be started manually by user request, or automatically. At 2004, the initial movement patterns can be set. The movement patterns can be set based on previously stored configurations, hard coded, or received as input parameters from the user at the start of the session. At 2006, milk flow data from sensors 504 can be monitored. If, after a certain amount of time, insufficient milk flow is detected at 2008, the movement patterns can be modified at 2010. Movement patterns can be modified to change the amount of pressure exerted by members 402. The pressure change can be localized, such that pressure is increased in some areas and decreased in others. The movement patterns can further be changed to modify the timing of burst patterns. One or more modifications can be made at one time, and in embodiments, the sequence of movement patterns to attempt can be configured by the user. After the movement patterns have be modified, control can return to 2006 to continue to monitor the milk flow. If the milk flow is sufficient, the session can continue at 2012. In embodiments, the current movement patterns can be saved for use in future sessions, or for data gathering purposes.

FIGS. 14-24 depict various alternative embodiments of compression mechanism 400, including alternative arrangements and configurations of members 402 and actuators 404. Compression mechanism 400 can provide mechanical compression provided by one or more of a worm gear system, a pulley tensioning system, a cable tensioning weave, and/or a linkage system that translates rotational and linear motion.

Figure 14:
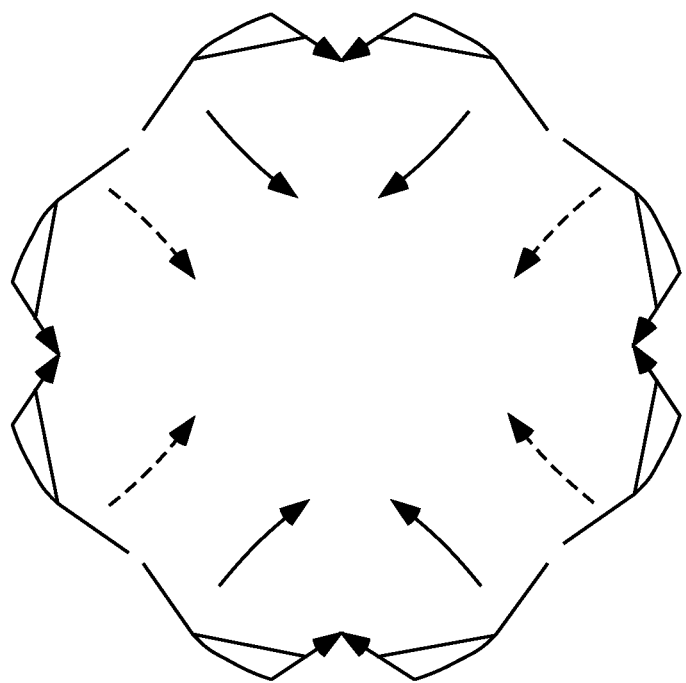
FIG. 14 is a plan view depicting a compression mechanism, according to an embodiment.
Figure 15:
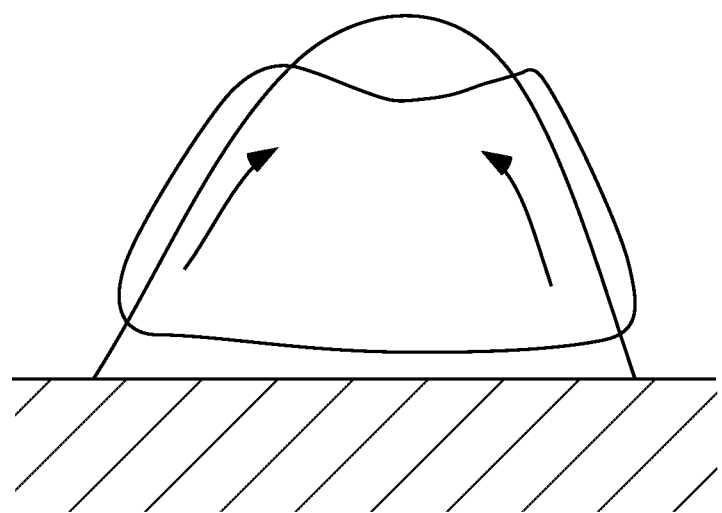
FIG. 15 is a plan view depicting a compression mechanism, according to an embodiment.

FIG. 14 is an anterior view depicting a winged embodiment of compression mechanism 400. Members 402 can comprise two-part wings and be operably coupled to juxtaposed electromagnetic actuators. When energized, electromagnetic actuators 404 can be mutually repelled, such that members 402 are urged radially inward. In embodiments, members 402 and actuators 404 can be arranged such that electromagnetic attraction results in inward pressure. FIG. 15 is an side view depicting a sleeve based compression mechanism 400. Members 402 be arranged within the sleeve to provide axially forward pressure to breast 10.

Figure 16A:
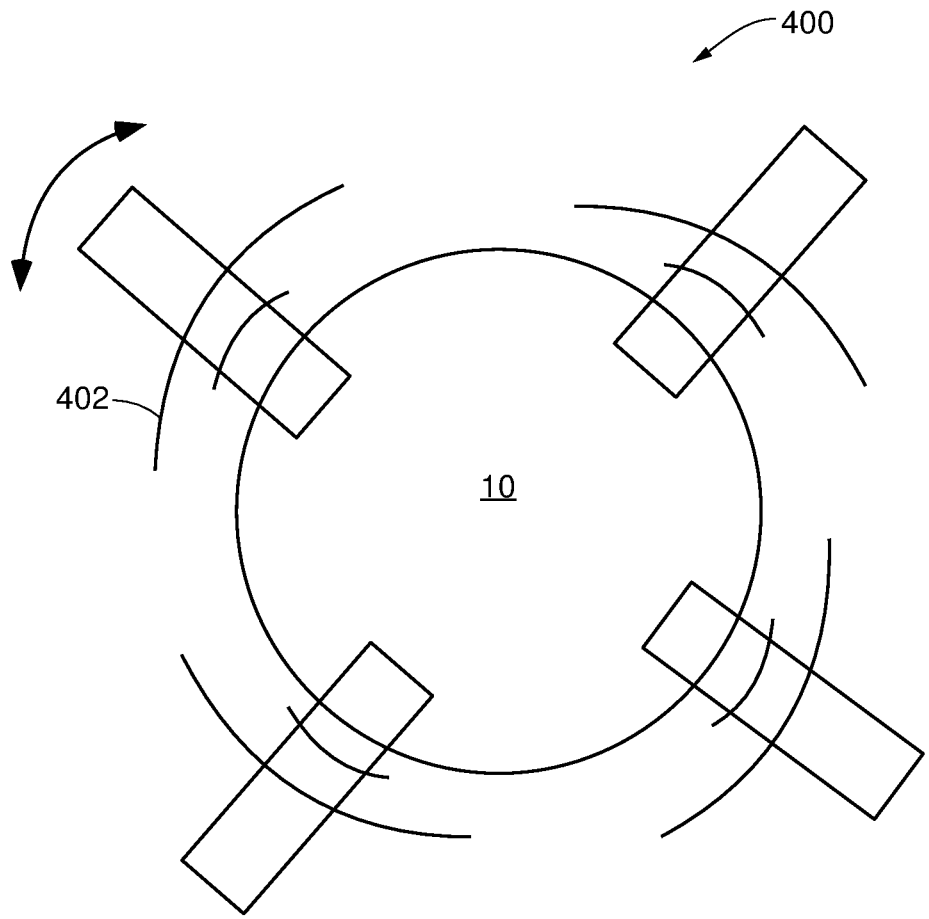
FIG. 16A is a plan view depicting a compression mechanism, according to an embodiment.
Figure 16B:
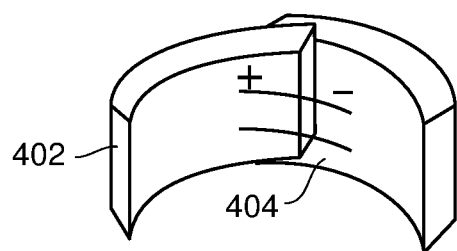
FIG. 16B is a perspective view depicting a compression mechanism, according to an embodiment.

FIG. 16A is an anterior view depicting a linear bearing based embodiment. Linear bearings can be arranged along one or more circular magnetic tracks. Members 402 can be operably coupled to the bearing such that they move circumferentially around the breast when the track is magnetically activated. FIG. 15B is a perspective view depicting an embodiment where magnetic actuators can urge members along/into each other.

Figure 17:
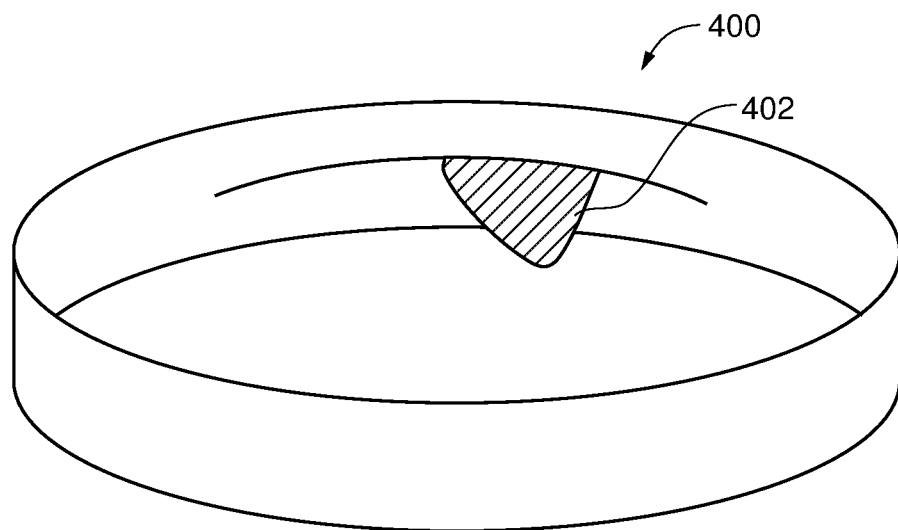
FIG. 17 is a perspective view depicting a compression mechanism, according to an embodiment.

FIG. 17 is a perspective view depicting a cam-projection based embodiment. Members 402 can comprise cam-like projections inward from circumferential a track.

Figure 18:
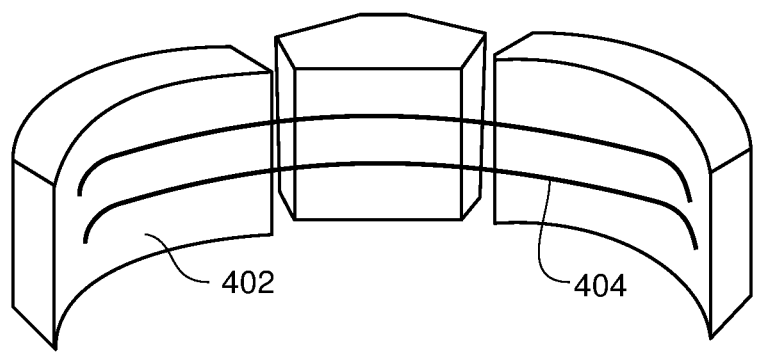
FIG. 18 is a perspective view depicting a compression mechanism, according to an embodiment.

As depicted in FIG. 18, actuators 404 can comprise tightenable tensioners (such as cables). Tensioners can be tightened circumferentially to shift members 402 together and/or into/across each other via tracks/slides results to result in a decrease in diameter.

Figure 19A:
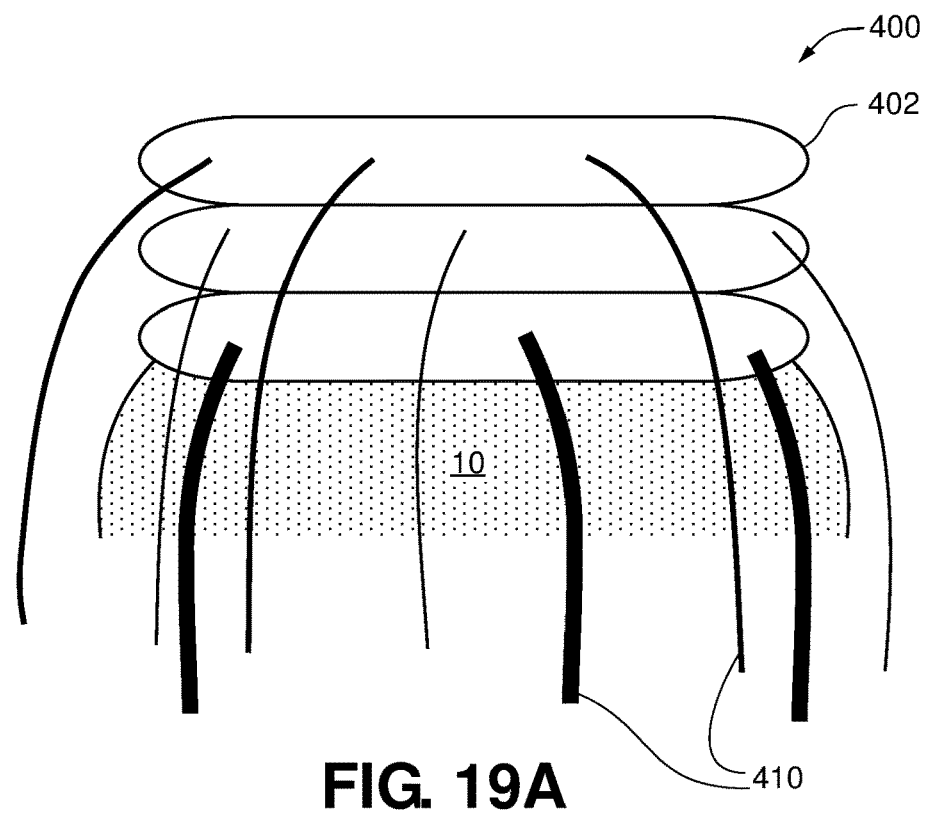
FIG. 19A is a plan view depicting a compression mechanism, according to an embodiment.
Figure 19B:
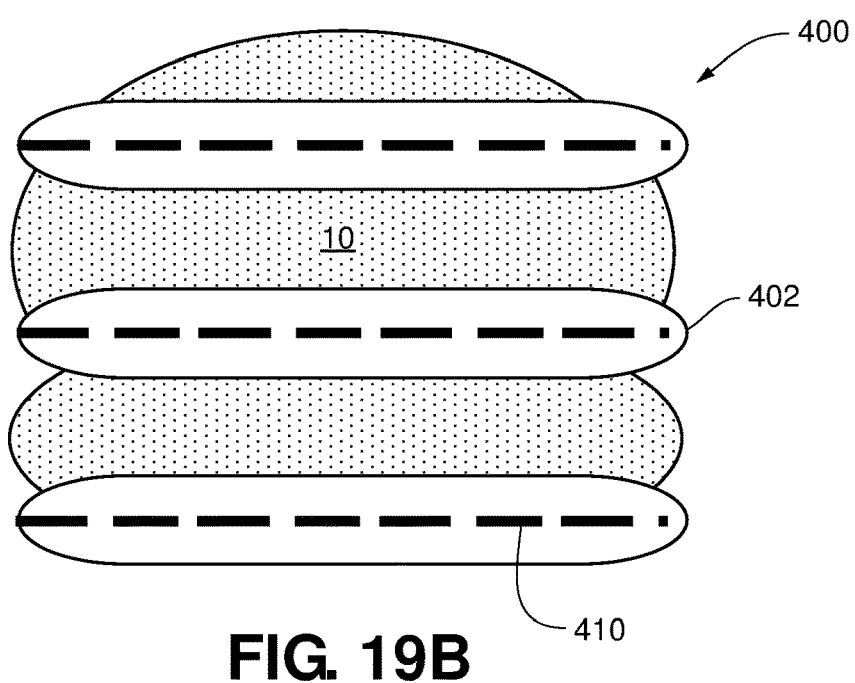
FIG. 19B is a plan view depicting a compression mechanism, according to an embodiment.

FIGS. 19A and 19B are side views depicting a ring based embodiment. Members 402 can comprise disc, rings, or plates, which can be pulled axially toward or away from the chest wall by actuator cables. The interlocking/separable members 402, can move individually or in synchrony about a z-axis (normal to the chest wall). Members 402 can be 360 degrees or less, and circular, oblong, or oval. Actuators 404 can comprise tensioner cables and/or rods. Two or more members can be connected to cables that are embedded into material, pockets, and/or tracks, enabling coverage of cables and therefore avoidance of pinch points while in motion. Rotational movement about the z-axis can allow for cables to twist and pull solid bodies in toward center of breast. In an embodiment, members 402 can be interlocked to enable dual-motion/or dual-motion/rotation.

Figure 20A:
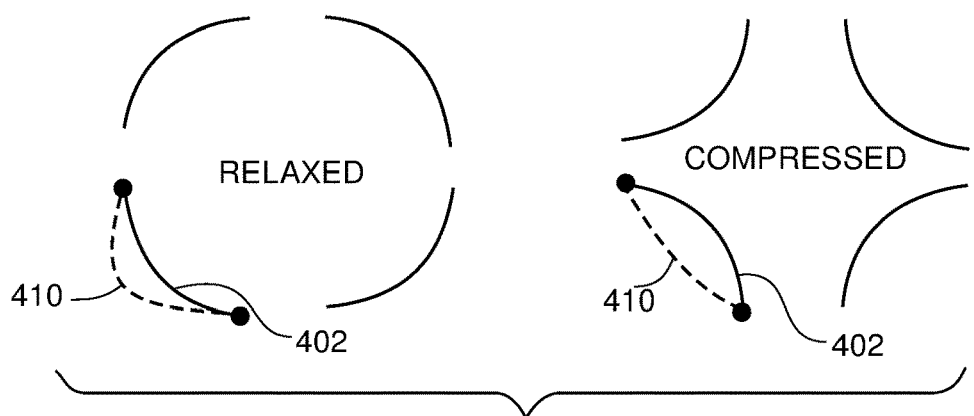
FIG. 20A is a plan view depicting a compression mechanism, according to an embodiment.
Figure 20B:
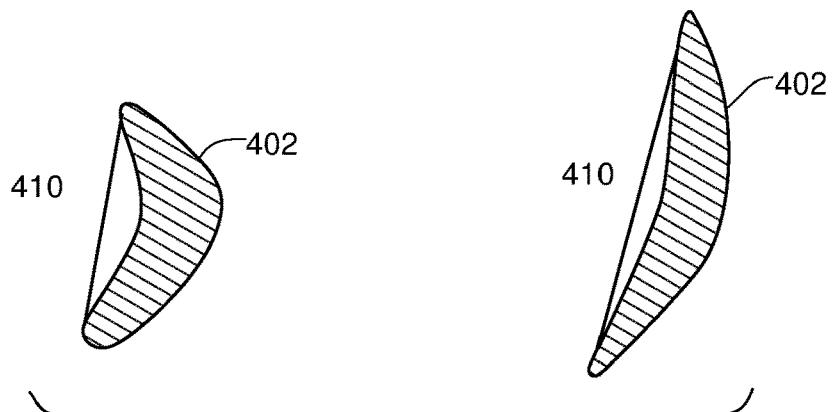
FIG. 20B is a perspective view depicting a compression mechanism, according to an embodiment.
Figure 20C:
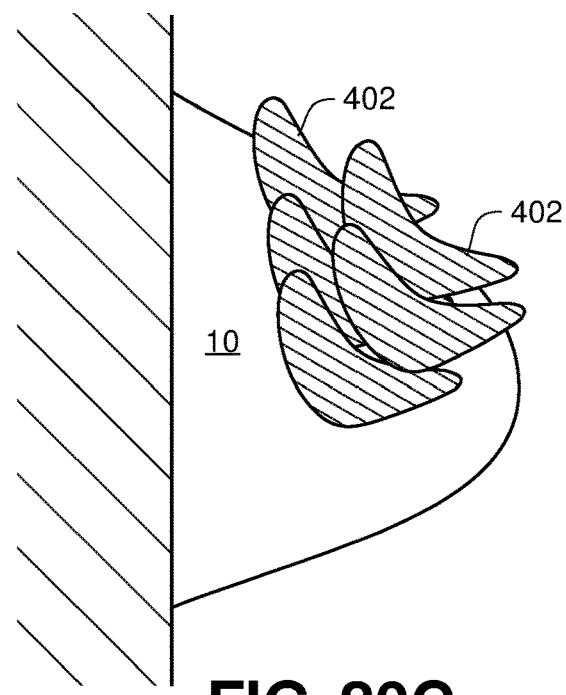
FIG. 20C is a perspective view depicting a compression mechanism, according to an embodiment.

FIGS. 20A-20C depict an additional tension cable embodiment. Members 402 can be manipulated by cables 410 of actuators 404 to move between relaxed and compressed states. While, as depicted tightening of cables 410 results in members 402 moving into a compressed state, members 402 and cables 410 can be arranged such that tightening results in relaxation of members 402.

Figure 21A:
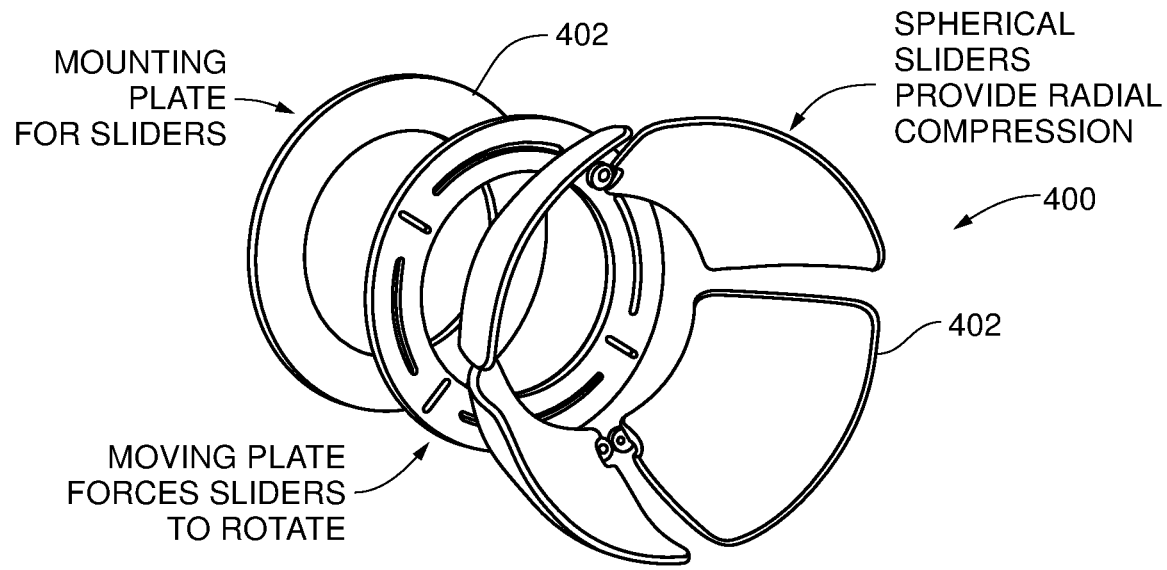
FIG. 21A is a perspective view depicting a compression mechanism, according to an embodiment.
Figure 21B:
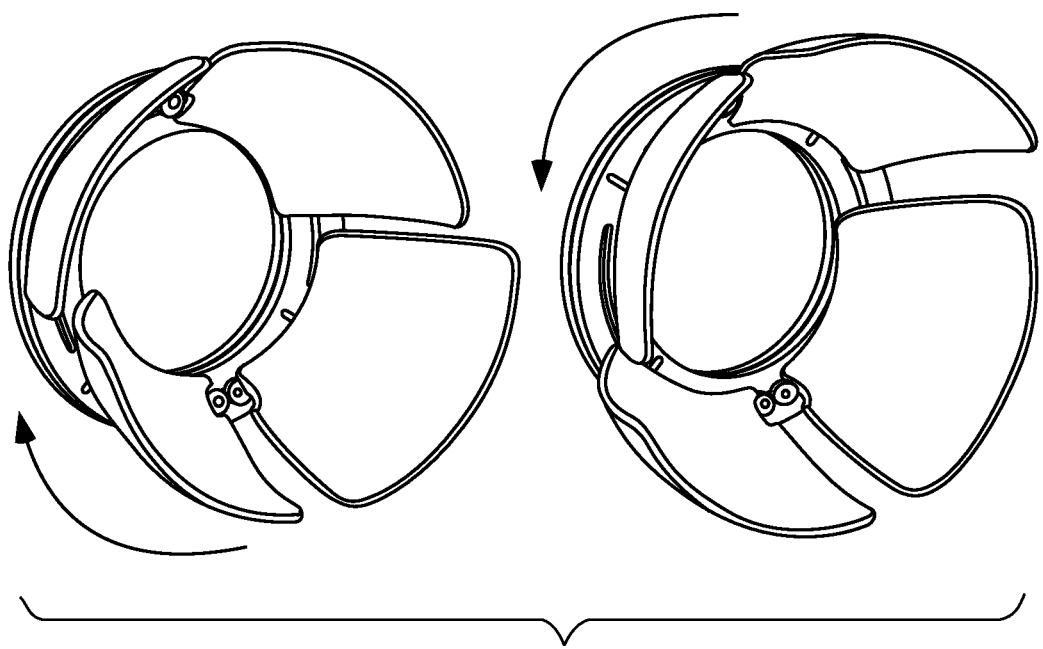
FIG. 21B is a perspective view depicting a compression mechanism, according to an embodiment.

FIGS. 21A and 21B depict a spherical slider embodiment. Members 402 can be semi-spherical plates which can be operably coupled to a track for circumferential movement around breast tissue.

Figure 22A:
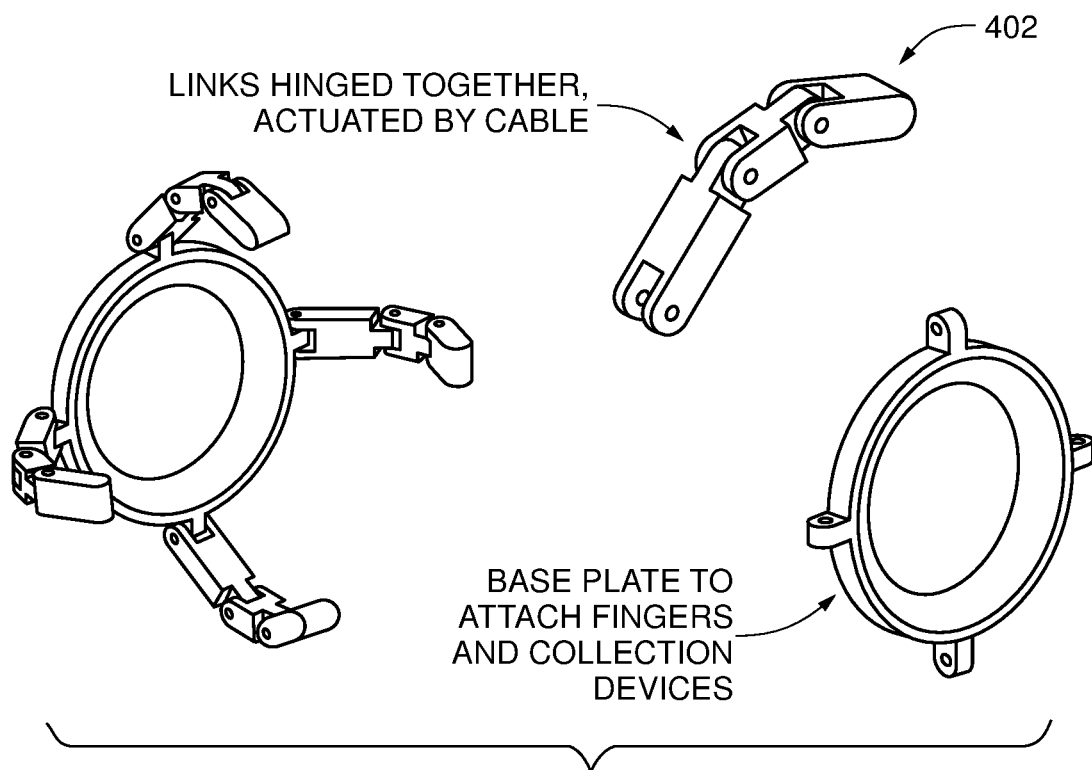
FIG. 22A is a perspective view depicting a compression mechanism, according to an embodiment.
Figure 22B:
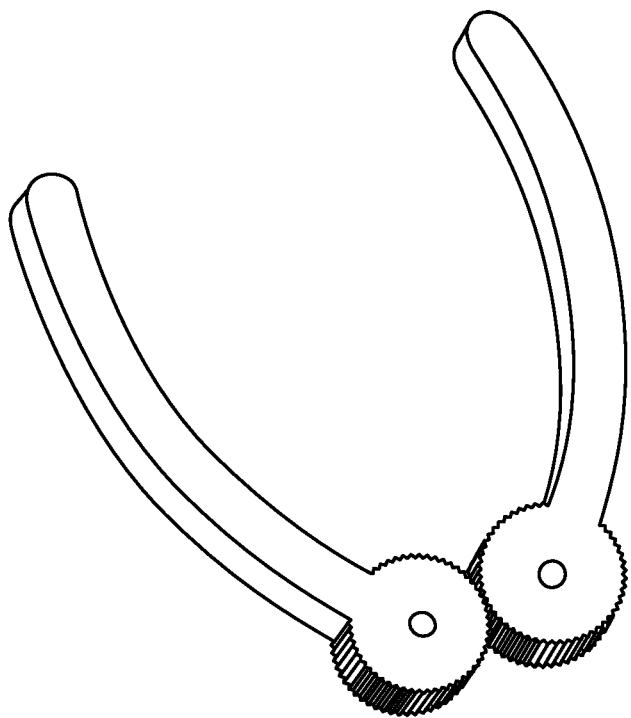
FIG. 22B is a perspective view depicting a compression mechanism, according to an embodiment.

FIGS. 22A and 22B depict a finger-like embodiment. Members 402 can comprise segmented fingers. The fingers can be actuated by cables, linkages, or individual motors, in embodiments. The fingers can be operably coupled to a ring, which can also comprise collection mechanism 118.

Figure 23A:
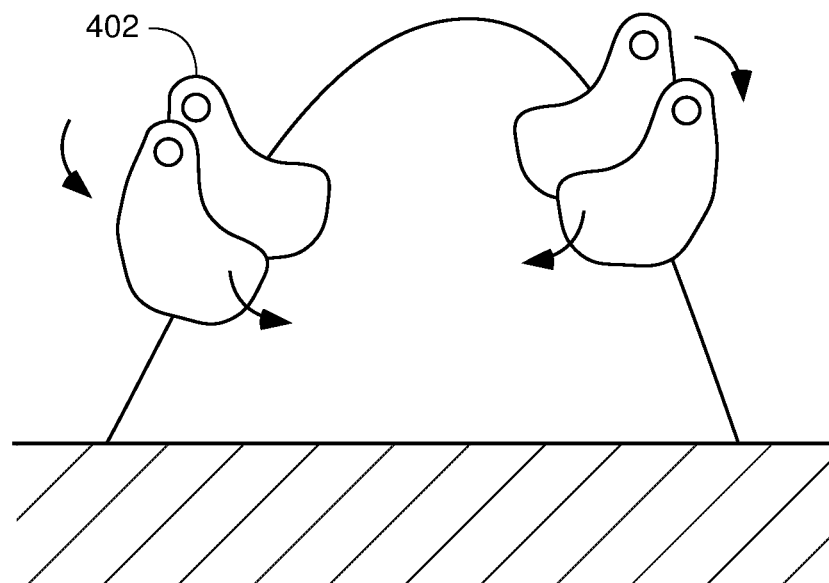
FIG. 23A is a plan view depicting a compression mechanism, according to an embodiment.
Figure 23B:
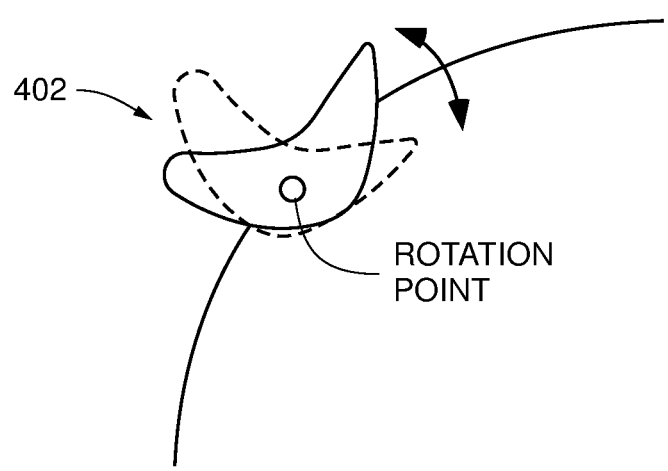
FIG. 23B is a perspective view depicting a compression mechanism, according to an embodiment.

FIGS. 23A and 23B depict rocker based embodiments. Members 402 can rockers that can be urged by multi-phased rocker arms for compression. Members 402 can each comprise individual rotation points, and can be actuated via electromagnets, cables, or other actuation methods discussed herein.

Figure 24A:
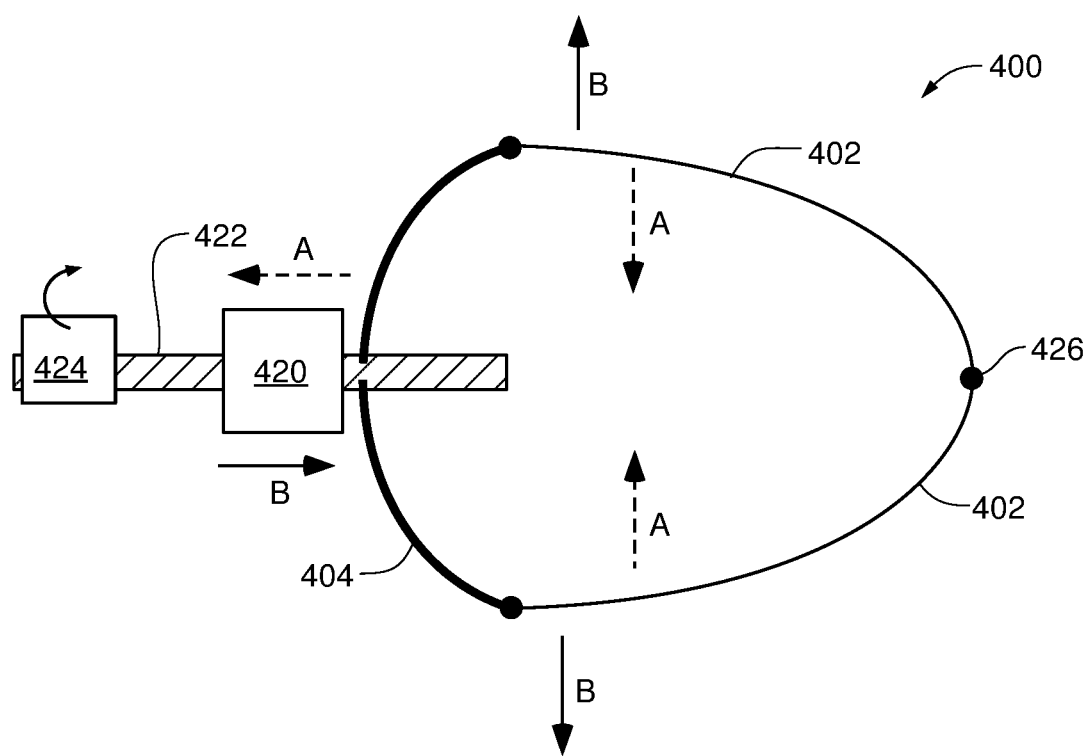
FIG. 24A is a plan view depicting a compression mechanism, according to an embodiment.
Figure 24B:
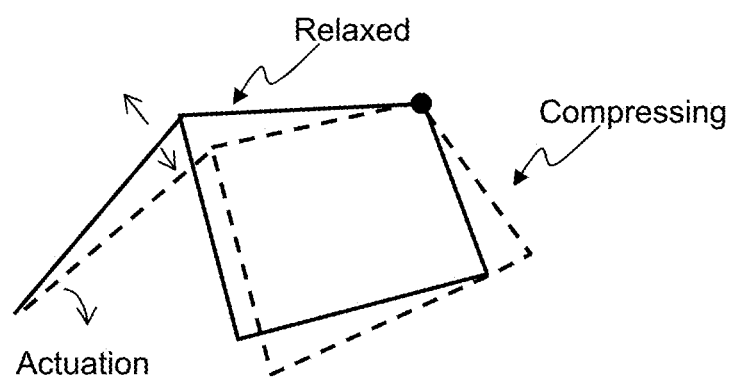
FIG. 24B is a perspective view depicting a compression mechanism, according to an embodiment.
Figure 24C:
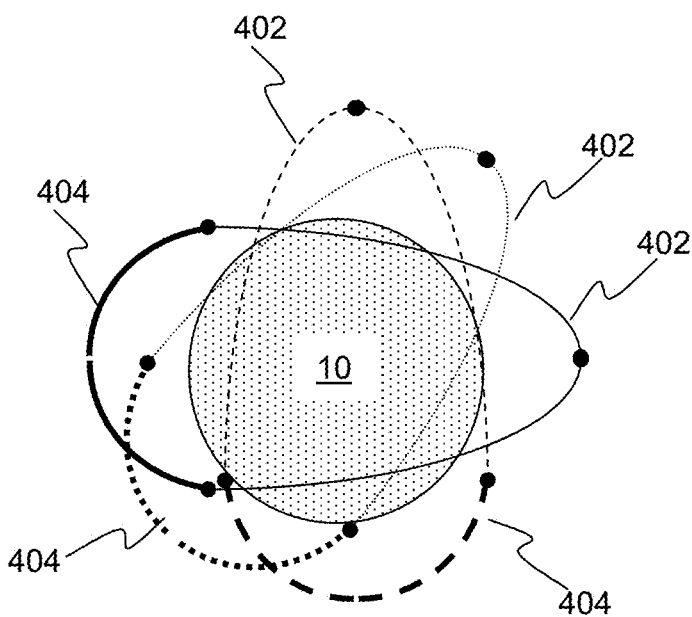
FIG. 24C is a plan view depicting a compression mechanism, according to an embodiment.

As depicted in FIGS. 24A-24C, actuators 404 can comprise multiple layered linkage systems to synchronize the compressive phase between groups of actuators 404. The corresponding members can therefore be locked stationary, or moving based on actuation. In embodiments, the linkage systems can comprise four-bar linkages. The bars of the linkage system can be members 402. As depicted in FIG.

24A, a collar 420 can be driven along a shaft 422 by a motor 424 or other means. Shaft 422 can be flexible, fully rigid, or partially rigid. Members 402 can be attached at a hinge point 426. Movement of collar 420 along shaft can induce a clamping action in members 402. Multiple actuators 404 can be provided and arranged radially around the breast 10.

Actuators 404 can comprise shapeable material inserts to fit to breast surface, thereby reducing clearance between the device starting position (relaxed or compressed) and the corresponding active position (compressed or relaxed). Actuators 404 can comprise ball and/or pivot joint connections. This can enable a more comfortable fit, due to the additional degrees of freedom. Actuators 404 can be embedded in wearable garment 102, and/or polymer materials within inserts 108. Actuators can be operably coupled to motor 424 by a tiered gear system which can provide synchrony between each group of actuators.

Embodiments of the present disclosure can enable mothers to extract breast milk discreetly, and can mimic many of the physiologic mechanisms that occur during breastfeeding. Many infants do not exclusively receive breast milk for nutrition as recommended by the World Health Organization, the Center for Disease Control and the American Academy of Pediatrics because the current system of breast pumping for working mothers presents significant barriers. These barriers account for the second most common reason for women to stop breast pumping. This device aims to improve the work-life balance for women so that they can continue to excel at work while still providing breast milk to their infants. Additionally, this device aims to increase the proportion of infants who are exclusively nourished with breast milk at 6 months of age.

In contrast to traditional breast pumps, embodiments use warmth to stimulate, and can provide mechanical compression as a mechanism of expression. Embodiments can mimic the infant interaction at the nipple while avoiding reliance on a suction mechanism for expression. Embodiments further provide for configurable parameters for compression force including specific patterns and locations of compression. Because embodiments can be integrated into a wearable garment they can remain discrete and allow for the hands-free extraction of breast milk.

Embodiments of the present disclosure include a method for collecting milk from a lactating breast, the method comprising receiving at a controller, a strain threshold parameter; monitoring, with at least one sensor arranged proximate the breast, a strain or displacement of the breast; in response to detecting the strain or displacement of the breast being above the threshold parameter, automatically collecting the milk from the breast by selectively applying pressure to a region of the breast by controlling a plurality of manipulable members operably coupled to actuators in an extraction mechanism and arrangeable circumferentially about the breast to move according to a movement pattern, the movement pattern configured to stimulate the breast to induce a flow of milk from the breast; and receiving the flow of milk in a storage compartment of a collection mechanism operably coupleable to the extraction mechanism proximate the nipple of the breast. The method can further comprise determining if the collection mechanism is operably coupled to the extraction mechanism before collecting the milk from the breast.

In an embodiment a lactation system can comprise at least one extraction mechanism comprising a compression mechanism comprising a plurality of manipulable members, operably coupled to actuators and arrangeable circumferentially about a breast of a user such that each member can be actuated to selectively apply pressure to a region of the breast, and a collection mechanism, removably coupleable to the compression mechanism proximate the nipple of the user and comprising a storage compartment to receive and store a flow of milk from the breast; and a controller operably coupleable to the actuators to cause the members to move according to a movement pattern, the movement pattern configured to stimulate the breast to induce the flow of milk from the breast.

An embodiment further comprises a wearable garment, the wearable garment comprising: an inner structure configured to be removably coupled to the at least one extraction mechanism; and an outer cover comprising padding and arrangeable to conceal the at least one extraction mechanism.

An embodiment further comprises a stimulation mechanism comprising a heating element configured to warm mammary glands within the breast to a temperature between 35° Celsius and 42° Celsius. In one embodiment, the stimulation mechanism comprises a plurality of heating elements arranged an outer cover arrangeable to conceal the at least one extraction mechanism.

In an embodiment, the actuators comprise one or more cables operably coupled to a series of linkages configured to move axially between the chest wall and the nipple of the user.

The members can be operably coupleable to an annular base that is arrangeable about the breast proximate the chest wall of the user. Each of the members is rotatable about an individual axis. In an embodiment, the movement pattern comprises mechanically compressing the breast at a pressure between 0 mmHg and 215 mmHg. The movement pattern can comprise mechanically compressing the breast at a pressure between 20 mmHg and 40 mmHg.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

In one embodiment, the control system 500 and/or its components or subsystems can include computing devices, microprocessors, modules and other computer or computing devices, which can be any programmable device that accepts digital data as input, is configured to process the input according to instructions or algorithms, and provides results as outputs. In one embodiment, computing and other such devices discussed herein can be, comprise, contain or be coupled to a central processing unit (CPU) configured to carry out the instructions of a computer program. Computing and other such devices discussed herein are therefore configured to perform basic arithmetical, logical, and input/output operations.

Computing and other devices discussed herein can include memory. Memory can comprise volatile or non-volatile memory as required by the coupled computing device or processor to not only provide space to execute the instructions or algorithms, but to provide the space to store the instructions themselves. In one embodiment, volatile memory can include random access memory (RAM), dynamic random access memory (DRAM), or static random access memory (SRAM), for example. In one embodiment, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the disclosure.

In one embodiment, the system or components thereof can comprise or include various modules or engines, each of which is constructed, programmed, configured, or otherwise adapted to autonomously carry out a function or set of functions. The term "engine" as used herein is defined as a real-world device, component, or arrangement of components implemented using hardware, such as by an application specific integrated circuit (ASIC) or field-10 programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Moreover, reference in the specification to "one embodiment," "an embodiment," or "some embodiments" means that a particular feature, structure, or characteristic, described in connection with the embodiment, is included in at least one embodiment of the teaching. The appearances of the phrase "in one embodiment" in various places in the specification are not necessarily all referring to the same embodiment.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. A lactation system comprising:
    a wearable garment comprising an inner structure configured to be removably coupled to at least one insert and an outer cover arrangeable to conceal the at least one insert;
    a stimulation mechanism comprising a heating element configured to warm mammary glands within a breast of a user to a temperature between 35° Celsius and 42° Celsius;
    each at least one insert comprising:
        a compression mechanism comprising a plurality of manipulable members, each of the plurality of manipulable members operably coupled to an actuator and arrangeable circumferentially about the breast such that each of the plurality of manipulable members can be actuated to selectively apply pressure to a region of the breast, and
        a collection mechanism, operably coupleable to the compression mechanism configured to be proximate a nipple of the user and comprising a storage compartment to receive and store a flow of milk from the breast; and
    a controller operably coupleable to the actuators to cause the plurality of manipulable members to move according to a movement pattern, the movement pattern configured to stimulate the breast to induce the flow of milk from the breast, wherein the movement pattern comprises mechanically compressing the breast in a burst pattern comprising applying pressure to locations at opposite positions around the breast, and wherein the burst pattern comprises repeatedly applying an upper pressure of about 200 mmHg for about one second and a lower pressure of about 20 mmHg for about three to seven seconds.

2. The lactation system of claim 1, wherein the movement pattern comprises mechanically compressing the breast at a pressure between 0 mmHg and 215 mmHg.

3. The lactation system of claim 1, wherein the burst pattern comprises repeatedly applying the lower pressure for about two to four seconds.

4. The lactation system of claim 1, wherein the movement pattern comprises repeating the burst pattern at least five times.

5. The lactation system of claim 1, further comprising at least one sensor for detecting the flow of milk and wherein the controller is configured to modify the movement pattern based on at least the flow of milk.

6. The lactation system of claim 1, wherein each actuator comprises at least one shape-memory alloy element configured to contract the actuator based on a received control signal.

7. The lactation system of claim 1, further comprising an external device coupleable to the controller to provide operational parameters to configure the movement pattern.

8. The lactation system of claim 7, wherein the external device comprises a user interface configured to: receive parameters from the user and display data received from one or more sensors to the user.

9. The lactation system of claim 1, wherein the storage compartment comprises a connection adapted to interface with an artificial nipple for feeding an infant.

* * * * *